(12) United States Patent
Ding et al.

(10) Patent No.: US 10,073,091 B2
(45) Date of Patent: Sep. 11, 2018

(54) LATERAL FLOW ASSAY DEVICE

(71) Applicant: ORTHO-CLINICAL DIAGNOSTICS, INC., Raritan, NJ (US)

(72) Inventors: Zhong Ding, Pittsford, NY (US); Philip C. Hosmier, Rochester, NY (US); Edward R. Scalice, Penfield, NY (US); Daniel P. Salotto, Rochester, NY (US); David A. Heavner, Fairport, NY (US)

(73) Assignee: Ortho-Clinical Diagnostics, Inc., Raritan, NJ (US)

( * ) Notice: Subject to any disclaimer, the term of this patent is extended or adjusted under 35 U.S.C. 154(b) by 357 days.

(21) Appl. No.: 14/819,893

(22) Filed: Aug. 6, 2015

(65) Prior Publication Data

US 2016/0041163 A1  Feb. 11, 2016

Related U.S. Application Data

(60) Provisional application No. 62/035,083, filed on Aug. 8, 2014.

(51) Int. Cl.
*G01N 33/53* (2006.01)
*G01N 33/558* (2006.01)
(Continued)

(52) U.S. Cl.
CPC .......... *G01N 33/558* (2013.01); *G01N 21/77* (2013.01); *G01N 33/5306* (2013.01); *G01N 33/536* (2013.01); *G01N 2021/7763* (2013.01)

(58) Field of Classification Search
None
See application file for complete search history.

(56) References Cited

U.S. PATENT DOCUMENTS 4,233,029 A  11/1980  Columbus
4,426,451 A   1/1984  Columbus
(Continued)

FOREIGN PATENT DOCUMENTS

CN  101623660 A  1/2010
CN  102414561 A  4/2012
(Continued)

OTHER PUBLICATIONS

International Search Report and Written Opinion for PCT/US2015/044123; dated Dec. 7, 2015; 12 pages.
(Continued)

*Primary Examiner* — Rebecca L Martinez
(74) *Attorney, Agent, or Firm* — K&L Gates LLP; Louis C. Cullman; Joseph Arand

(57) ABSTRACT

A lateral flow assay device includes a substrate having a top surface, as well as a sample receiving area disposed upon the top surface. At least one fluid flow path extends along the substrate from the sample receiving area, wherein the sample receiving area can be placed in contact with a peripheral reservoir formed at a sample addition area to draw sample therefrom in a controlled manner. The device can further include a reagent area that is designed to promote uniform dissolution of a deposited detection material by a sample moved through the device along the fluid flow path as well, as a flow channel configure to promote mixing of sample and reagent and an absorbing or wicking zone configured to affect various flow characteristics.

8 Claims, 15 Drawing Sheets

(51) Int. Cl.
*G01N 33/536* (2006.01)
*G01N 21/77* (2006.01)

(56) References Cited

U.S. PATENT DOCUMENTS

| | | | |
|---|---|---|---|
| 4,756,884 | A | 7/1988 | Hillman et al. |
| 5,087,556 | A | 2/1992 | Ertinghausen |
| 5,120,643 | A | 6/1992 | Ching et al. |
| 5,204,063 | A | 4/1993 | Allen |
| 5,399,486 | A | 3/1995 | Cathey et al. |
| 5,559,041 | A | 9/1996 | Kang et al. |
| 5,714,389 | A | 2/1998 | Charlton et al. |
| 6,228,660 | B1 | 5/2001 | May et al. |
| 6,372,542 | B1 | 4/2002 | Martin et al. |
| 6,381,072 | B1 | 4/2002 | Burger |
| 6,391,265 | B1* | 5/2002 | Buechler ............ B01D 61/18 210/496 |
| 6,663,833 | B1 | 12/2003 | Stave et al. |
| 6,733,682 | B1 | 5/2004 | Björkman et al. |
| 6,811,736 | B1 | 11/2004 | Ohman et al. |
| 6,884,370 | B2 | 4/2005 | Öhman et al. |
| 7,682,833 | B2 | 3/2010 | Miller et al. |
| 7,695,687 | B2 | 4/2010 | Delamarche et al. |
| 7,723,099 | B2 | 5/2010 | Miller et al. |
| 8,025,854 | B2 | 9/2011 | Ohman et al. |
| 8,597,590 | B2 | 12/2013 | Yue et al. |
| 8,623,296 | B2 | 1/2014 | Desmond et al. |
| 8,623,596 | B2 | 1/2014 | Gandini et al. |
| 8,722,423 | B2 | 5/2014 | Bergman et al. |
| 2004/0232074 | A1 | 11/2004 | Peters et al. |
| 2005/0042766 | A1 | 2/2005 | Ohman et al. |
| 2006/0216195 | A1 | 9/2006 | Blankenstein et al. |
| 2006/0239859 | A1 | 10/2006 | Ohman et al. |
| 2006/0285996 | A1 | 12/2006 | Ohman et al. |
| 2008/0213133 | A1 | 9/2008 | Wallace et al. |
| 2010/0165784 | A1 | 7/2010 | Jovanovich et al. |
| 2011/0003398 | A1 | 1/2011 | Mendel-Hartvig et al. |
| 2011/0011781 | A1* | 1/2011 | Blankenstein .... B01L 3/502715 210/205 |
| 2011/0053289 | A1 | 3/2011 | Lowe et al. |
| 2011/0189721 | A1 | 8/2011 | Deutsch |
| 2011/0300555 | A1 | 12/2011 | Raj et al. |
| 2012/0021951 | A1 | 1/2012 | Hess et al. |
| 2012/0028342 | A1 | 2/2012 | Ismagilov et al. |
| 2012/0070833 | A1 | 3/2012 | Wang et al. |
| 2012/0107851 | A1 | 5/2012 | Killard et al. |
| 2012/0135510 | A1 | 5/2012 | Gordon et al. |
| 2012/0177543 | A1 | 7/2012 | Battrell et al. |
| 2012/0328488 | A1 | 12/2012 | Puntambekar et al. |
| 2012/0329148 | A1 | 12/2012 | Hur et al. |
| 2013/0189672 | A1 | 7/2013 | Ding |
| 2013/0189673 | A1 | 7/2013 | Scalice et al. |
| 2013/0189796 | A1 | 7/2013 | Kanaley et al. |
| 2013/0210036 | A1 | 8/2013 | Kanaley et al. |
| 2013/0225791 | A1 | 8/2013 | Reichert et al. |
| 2013/0330713 | A1 | 12/2013 | Jakubowicz et al. |
| 2014/0140891 | A1 | 5/2014 | Fiering |
| 2014/0141527 | A1 | 5/2014 | Ding et al. |
| 2016/0038937 | A1 | 2/2016 | Ding et al. |

FOREIGN PATENT DOCUMENTS

| | | |
|---|---|---|
| EP | 0 057 110 A2 | 8/1982 |
| EP | 2 332 651 A2 | 6/2011 |
| EP | 2 618 151 A1 | 7/2013 |
| EP | 2 674 763 A2 | 12/2013 |
| JP | 2003-512624 | 4/2003 |
| WO | WO 01/29558 A1 | 4/2001 |
| WO | WO 03/103835 A1 | 12/2003 |
| WO | WO 2005/089082 A2 | 9/2005 |
| WO | WO 2005/118139 A1 | 12/2005 |
| WO | WO 2006/105110 A2 | 10/2006 |
| WO | WO 2006/137785 A1 | 12/2006 |
| WO | WO 2007/022026 A2 | 2/2007 |
| WO | WO 2007/149042 A1 | 12/2007 |
| WO | WO 2012/025637 A1 | 3/2012 |
| WO | WO 2012/103533 A2 | 8/2012 |
| WO | WO 2012/164552 A1 | 12/2012 |
| WO | WO 2013/154946 A1 | 10/2013 |

OTHER PUBLICATIONS

Japanese Office Action for JP 2017-506887; dated Jul. 11, 2017, 4 pages.
European Office Action for EP 15 753 804.2; dated Aug. 2, 2017; 2 pages.
Miniaturized technology for protein and nucleic acid point-of-care testing; Olasagasti et al.; Translational Research; vol. 160; Issue 5; Nov. 2012; pp. 332-345; 14 pages.
Industrial lab-on-a-chip: Design, applications and scale-up for drug discovery and delivery; Vladisavljević et al.; Advanced Drug Delivery Reviews; vol. 65, Issues 11-12, Nov. 15, 2013; pp. 1626-1663; 38 pages.
Finger-Actuated, Self-Contained Immunoassay Cassettes; Qui et al.; Biomed Microdevices; Dec. 2009; 22 pages.
Continuous flow microfluidic device for cell separation, cell lysis and DNA purification; Chen et al.; ScienceDirect; 2007; pp. 237-243; 7 pages.
Japanese Office Action for JP 2017-506887; dated Nov. 7, 2017; 2 pages.
Chinese Office Action for CN 201580054669.1; dated Oct. 30, 2017; 12 pages.

* cited by examiner

LATERAL FLOW ASSAY DEVICE

CROSS REFERENCE TO RELATED APPLICATIONS

This application claims priority under applicable portions of 35 U.S.C. § 119 to U.S. Patent Application Ser. No. 62/035,083, filed Aug. 8, 2014, and entitled: LATERAL FLOW ASSAY DEVICE, the entire contents of which are herein incorporated by reference.

TECHNICAL FIELD

This application relates generally to the field of analytical chemistry and more specifically to a lateral flow assay device having features designed to improve flow characteristics of an applied fluidic sample along at least one defined fluid flow path, as well as the overall effectiveness of the assay device, for example, for use in mainframe and point of care diagnostic apparatus.

BACKGROUND

There are several forms of assay devices presently found in the medical diagnostic field that are used for determining a specific analyte of a bodily fluid sample, such as whole blood, by reacting the fluid sample with at least one reagent and then determining an analyte or marker of interest. For example and referring to FIG. 1, there is shown a known lateral flow assay device 1 defined by a substrate 6, which is substantially planar and further defined by an upper or top surface 7, the substrate forming a support. A plurality of projections 12 extend upwardly from the top surface 7. These projections 12 are disposed in a predetermined spaced relation to one another and dimensioned so as to induce lateral capillary force upon a liquid sample that is introduced into the assay device 1. The assay device 1 is further defined by a plurality of areas or zones that are linearly disposed along at least one fluid flow path. More specifically, the assay device 1 includes a sample addition zone 2 adjacent at least one reagent zone 3, the reagent zone 3 having a detection material (not shown), such as a detection conjugate that is coated, impregnated or otherwise applied or deposited onto the projections 12. A flow channel 4 extends from the reagent zone 3 to an absorbing or wicking zone 5 that is disposed at the opposing end of the fluid flow path relative to the sample addition zone 2. Each of the above noted zones according to this design include a plurality of the projections 12 in order to induce lateral capillary flow through the assay device 1, and more specifically along the defined fluid flow path. Additional specifics relating to this lateral flow assay device can be found in U.S. Pat. No. 8,025,854 B2, WO2003/103835, WO2005/089082, WO2005/118139, and WO2006/137785, all of which are incorporated herein by reference in their entireties.

In terms of overall operation, a fluidic sample such as whole blood is initially applied to the sample addition zone 2 through a cover (not shown) or through direct application using a pipette (not shown) or other dispensing means, wherein sample is caused to move along the defined fluid flow path through the reagent zone 3 based on the capillary pressure exerted by the plurality of projections 12. The sample upon encountering the detection material in the reagent zone 3 which, upon contact, therewith produces a detectable signal, such as a color change that is visually perceivable. The sample, along with the gradually dissolved detection material, continues to migrate through the assay device 1 along the defined fluid flow path through the flow channel 4, the latter having at least one predetermined area or zone configured for detection by an instrument, such as a scanning fluorimeter, and wherein the sample continues to move along the fluid flow path to the absorbing zone 5. After a sufficient time to fill the absorbing zone 5, the assay is considered to be complete and a detectable result can be obtained at the predetermined detection area(s) using the detection instrument.

Another example or version of a lateral flow assay device 20 is illustrated in FIG. 2, the device 20 including a planar substrate 40 which can be made from a moldable plastic or other suitable non-porous material. The substrate 40 is defined by a top or upper surface 44, which is further defined by a plurality of discrete zones or areas including a sample receiving zone 48, a reagent zone 52, and an absorbing or wicking zone 60. According to this known device design, each of the above-noted zones are fluidically connected to one another in a linear fashion along a defined fluid flow path that further includes a flow channel 64, which can include at least one detection zone (not shown) and in which a plurality of projections (not shown), similar to those provided in the assay device 1 of FIG. 1, are disposed within at least one of the zones and/or the flow channel 64, the projections extending upwardly from the upper surface 44 of the substrate 40 and in which the projections may be provided in at least one or all of the disposed zones of the assay device 20 to promote sample flow.

The projections can be sufficiently dimensioned so as to spontaneously induce capillary flow without the need for additional structure (i.e., side walls, cover or lid) or the application of any externally applied forces. According to this design, a defined fluid flow path is created from the sample receiving zone 48 extending to the wicking zone 60 and in which the fluid flow path is at least partially open. In another embodiment, the assay device 20 can be entirely open. By "open" what is meant is that there is no cover or lid which is maintained at a distance that would contribute to capillary flow. Thus a lid, if present as physical protection for the flow path and the device 20, does not contribute to the capillary flow produced along the fluid flow path. In this known assay device 20, a hydrophilic foil layer 70 is adhesively or otherwise applied to the top of the projections in the wicking zone 60 in order to increase fluid flow in the assay device 20 and in which a plurality of vents 72 are further defined in the hydrophilic foil layer 70. A flow bridging structure 57 may be provided to further enable flow across an outer edge of the hydrophilic foil layer 70, as further discussed herein. An open lateral flow path is described including the defined projections in the following published application: WO2003/103835; WO2005/089082; WO2005/118139; WO2006/137785; and WO2007/149042 as well as U.S. Patent Application Publication No. 2014/0141527 A1, each of which are herein incorporated by reference in their entireties. More specifically, the extending projections each have a height (H), diameter (D) and a distance or distances between the projections (t1, t2) such that lateral capillary flow of an applied fluid, such as plasma, preferably human plasma, can be achieved. These relationships are further discussed in US Patent Application Publication No. 2006/0285996, which is further incorporated herein by reference in its entirety.

In use, the assay device 20 operates similarly to the assay device 1, FIG. 1, in which a sample is applied to the sample receiving zone 48, which causes sample to move under capillary force to the reagent zone 52 containing the deposited detection material. When wetted by the sample, the detection material may react, depending on the type of assay (e.g., competitive, sandwich, etc.) with the sample and dissolves, thereby producing a visually perceivable (colored) signal. The sample and the dissolved detection material advance along the defined fluid flow path along the flow channel 64 via the projections and under capillary force into the absorbing zone 60. When the absorbing zone 60 is filled with fluid, the assay is assumed to be completed and the assay results can be taken by a detection instrument (e.g., a fluorimeter) relative to the flow channel 64 and at least one detection zone 56.

Referring to FIG. 3, there is depicted yet another known lateral flow assay device 100 defined by a planar substrate 104 which can be made from a moldable plastic or other suitable non-porous material. A plurality of discrete zones or areas are defined in spaced relation along on a top surface of the substrate 104, the zones extending along a linear fluid flow path. These zones include a sample receiving zone 108, a reagent zone 112, a flow channel 116, which can contain at least one detection zone (not shown), and an absorbing or wicking zone 120, respectively. In this specific device version, the fluid flow path is defined by a folded configuration extending from the sample receiving zone 108 through a reagent zone 112 containing a deposited detection material, such as a detection conjugate or other suitable reagent. The fluid flow path further extends along the flow channel 116 of the device 100, the latter further extending to a wicking or receiving zone 120 that defines the opposite end of the folded lateral fluid flow path. According to this particular device configuration, two distinct folds are present, a first fold between the reagent zone 112 and a first or entry end of the flow channel 116 and a second fold between a second or exit end of the flow channel 116 and the wicking zone 120.

According to this particular design a plurality of projections, similar to those previously depicted in FIG. 1, extend upwardly from the top surface of the substrate 104 substantially defining the active zones defined within the bordering line of this device 100 wherein the projections are specifically designed dimensionally in terms of their height and diameters, as well as with relative interpillar spacings, so as to solely promote spontaneous lateral capillary flow along the defined fluid flow path between the sample addition zone 108 and the wicking zone 120. As discussed infra, this specific device design is referred to as an "open" system or device, meaning that side walls and a cover are not necessarily required to assist in the creation of capillary force and as described in the following: U.S. Patent Application Publication No. 2014/0141527 A1; WO 2003/103835, WO 2005/089082; WO 2005/118139; WO 2006/137785; and WO 2007/149042, previously incorporated by reference in their entireties. It will further be noted that a cover or lid can be optionally included; for example, a cover (not shown) can be added to the device as needed, the cover being spaced in relation to the projections so as not contribute to the lateral capillary flow of a sample liquid. It is has been determined, however, similar to that depicted in FIG. 2, that the addition of a hydrophilic foil or layer 130 directly onto at least a portion of the wicking zone 120 alone does contribute to the overall flow rate (process time) of an aspirated sample.

The operation of this lateral flow assay device 100 is similar to each of the prior versions described. A fluidic sample, such as whole blood, is applied to the device 100 at the sample receiving area 108 such as through a cover (not shown) having an aperture (not shown) and separation filter (not shown). Upon contact with the projections of the sample receiving area 108, the sample is caused to move under capillary force along the fluid flow path through the reagent zone 112 in which the sample dissolves the deposited detection material to produce a visually perceivable signal. The sample and dissolved detection material then advance along the folded flow channel 116 to the absorbing zone 120, as further drawn due to the influence of the hydrophilic foil cover 130. Once it has been determined that the absorbing zone 120 is filled with sample, the detection instrument (not shown) can be used to determine analyte results through scanning or other means along the flow channel 116, which includes at least one detection area.

According to certain aspects, the fluid flow path of the assay device can alternatively include a porous material, e.g., nitrocellulose, in lieu of projections and define at least a portion of the flow path capable of supporting capillary flow. Examples include those shown in U.S. Pat. Nos. 5,559,041, 5,714,389, 5,120,643, and 6,228,660, all of which have been incorporated herein by their entireties.

An exemplary design of yet another known lateral flow assay device 300 is depicted in FIG. 4. This assay device 300 is defined by a planar substrate 304, which is made from a non-porous material, such as a molded plastic. As in the prior described assay devices, a plurality of zones or areas are disposed a defined fluid flow path. More specifically, a sample receiving zone 308 receives sample from a liquid dispenser, such as a pipette or other suitable means (not shown). The sample (e.g., whole blood) is typically deposited onto the top of the sample addition zone 308 through a cover (not shown) having an aperture (not shown). The sample receiving zone 308 is capable of transporting the dispensed liquid sample from the point when the sample is deposited to a pair of parallel spaced reagent zones 312, 313 through an optional filter and adjacent reagent addition zone 315, preferably through capillary flow. The capillary flow inducing structure can include porous materials, such as nitrocellulose, or preferably through a plurality of projections, such as micro-pillars or microposts that can spontaneously induce capillary flow through the assay device 300, in the manner previously described and shown in FIG. 1 and the prior incorporated US Patent Application Publication No. 2014/0141527 A1; WO 2003/103835, WO 2005/089082; WO 2005/118139; WO 2006/137785; and WO 2007/149042. A separation filter (not shown) or filter material (not shown) can be also be placed within the sample addition zone 308 to filter particulates from the sample or to filter red blood cells from blood so that plasma can travel through the assay device 300 as a filtrate.

As noted and located between the sample addition zone 308 and a folded portion of the flow channel 317 are the pair of adjacent reagent zones 312, 313, which are aligned in parallel relation herein. For purposes of the lateral flow assay devices herein described, including the improved versions, the reagent zones 312, 313 can include reagent(s) integrated into this analytical element and are generally reagents useful in the reaction—binding partners such as antibodies or antigens for immunoassays, substrates for enzyme assays, probes for molecular diagnostic assays, or are auxiliary materials such as materials that stabilize the integrated reagents, materials that suppress interfering reactions, and the like. Generally, one of the reagents useful in the reaction bears a detectable signal as previously discussed herein. In some cases, the reagents may react with the analyte directly or through a cascade of reactions to form a detectable signal such as a colored or fluorescent molecule. In this device design, the reagent zones 312, 313 each include a quantity of deposited conjugate material. The term "conjugate" as used herein means any moiety bearing both a detection element and a binding partner.

For purposes of this description throughout, a "detection element" is an agent which is detectable with respect to its physical distribution and/or the intensity of the signal it delivers, such as but not limited to luminescent molecules (e.g., fluorescent agents, phosphorescent agents, chemiluminescent agents, bioluminescent agents and the like), colored molecules, molecules producing colors upon reaction, enzymes, radioisotopes, ligands exhibiting specific binding and the like. The detection element, also referred to as a label, is preferably chosen from chromophores, fluorophores, radioactive labels and enzymes. Suitable labels are available from commercial suppliers, providing a wide range of dyes for the labeling of antibodies, proteins and nucleic acids. There are, for example, fluorophores spanning practically the entire visible and infrared spectrum. Suitable fluorescent or phosphorescent labels include for instance, but are not limited to, fluoroceins, Cy3, Cy5 and the like. Suitable chemiluminescent labels include but are not limited to acridinium esters, or enzymes such as peroxidase or alkaline phosphatase coupled with suitable substrates such as luminol, dioxetane and the like.

Similarly, radioactive labels are commercially available, or detection elements can be synthesized so that they incorporate a radioactive label. Suitable radioactive labels include but are not limited to radioactive iodine and phosphorus; e.g., $^{125}$I and $^{32}$P.

Suitable enzymatic labels include, but are not limited to horseradish peroxidase, beta-galactosidase, luciferase, alkaline phosphatase and the like. Two labels are "distinguishable" when they can be individually detected and preferably quantified simultaneously, without significantly disturbing, interfering or quenching each other. Two or more labels may be used, for example, when multiple analytes or markers are being detected.

The binding partner is a material that can form a complex that can be used to determine the presence of or an amount of an analyte. For example, in a "sandwich" assay, the binding partner in the conjugate can form a complex including the analyte and the conjugate and that complex can further bind to another binding partner, also called a capture element, integrated into the detection zone. In a competitive immunoassay, the analyte will interfere with binding of the binding partner in the conjugate to another binding partner, also called a capture element, integrated into the detection zone. Example binding partners included in conjugates include antibodies, antigens, analyte or analyte-mimics, protein, etc.

Referring back to FIG. 4 and located in the fluid flow path, before or after the reagent zone 312 and before the detection zone is an optional reagent addition zone 315. The reagent addition zone 315 can allow the addition of a reagent externally from the device 300. For example, the reagent addition zone 315 may be used to add an interrupting reagent that can be used to wash the sample and other unbound components present in the fluid flow path into a wicking (or absorbing) zone 324. In a preferred embodiment, the reagent addition zone 315 is located immediately downstream from the reagent zones 312, 313.

Still referring to FIG. 4 and downstream from the reagent zones 312, 313 and the optional reagent addition area 315 and along the lateral folded fluid path defined by the flow channel 317 is at least one detection zone, which is in fluid communication with the reagent zones 312, 313. The detection zone(s) and/or the flow channel 317 may include a plurality of projections, such as those as described above and shown in FIG. 1. These projections are preferably integrally molded into the substrate 304 from an optically transparent plastic material such as Zeonor, such through an injection molding or embossing process. The width in the flow channel 317 in the detection zone according to this specific device design is typically on the order of about 0.5 mm-about 4 mm and preferably on the order of about 2 mm, although others can be prepared on the order of about 1 mm, provided sufficient signal for a suitable detection instrument, such as a fluorimeter, can be read even if the reagent plume does not cover the entire width of the detection zone.

For purposes of this description throughout, the at least one detection zone is disposed anywhere along the flow channel 317 where any detectable signal can be read, although preferably the detection zone is located at about the center of the axial length of the flow channel 317 In a preferred embodiment and attached to the projections in the at least one detection zone are capture elements. The capture elements can hold binding partners for the conjugate or complexes containing the conjugate, as described above depending on the assay (e.g., competitive, sandwich). For example, if the analyte is a specific protein, the conjugate may be an antibody that will specifically bind that protein to a detection element such as fluorescence probe. The capture element could then be another antibody that also specifically binds to that protein. In another example, if the marker or analyte is DNA, the capture molecule can be, but is not limited to, synthetic oligonucleotides, analogues, thereof, or specific antibodies. Other suitable capture elements include antibodies, antibody fragments, aptamers, and nucleic acid sequences, specific for the analyte to be detected. A non-limiting example of a suitable capture element is a molecule that bears avidin functionality that would bind to a conjugate containing a biotin functionality. Multiple detection zones can be used for assays that include one or more markers. In the event of multiple detection zones, the capture elements can include multiple capture elements, such as first and second capture elements. The conjugate can be pre-deposited on the assay device 300, such as by coating or by deposition in the reagent zones 312, 313. Similarly, the capture elements can be pre-deposited on the assay device 300 on the at least one detection zone. Preferably, both the detection and capture elements are pre-deposited on the assay device 300, or on the reaction zones 312, 313 and detection zone(s), respectively.

For purposes of background, a brief treatment of the general process of the known lateral flow assay device 300 will now be generally discussed. After a predetermined quantity of sample has been delivered to the sample addition zone 308, the sample will be caused to migrate laterally along the defined flow path into the parallel disposed pair of reagent zones 312, 313. The sample will continue to flow under capillary action according to this version of device and interact with the detection material impregnated within the projections of the reagent zones 312, 313. As the sample interacts, the detection material begins to dissolve in which a resultant detectable signal is contained within the fluid flow, which is subsequently carried into the adjacent reagent addition zone 315. Alternatively and in lieu of the reagent zones, 312, 313, the sample can be combined with the reagent having the detection material prior to adding to the sample addition zone 308. According to this version, the detection material includes the conjugate having both the detection element and binding partner, in which case the perceived signal is often referred to as a "conjugate plume" and produces a fluorescent signal.

Downstream from the detection zone 318 and along the folded fluid path 317 is the wicking zone 324 in fluid communication with the detection zone. As in the case of prior lateral flow assay devices, the wicking zone 324 is an area of the assay device 300 with the capacity of receiving liquid sample and any other material in the flow path, e.g. unbound reagents, wash fluids, etc. The wicking or absorbing zone 324 provides a capillary force to continue moving the liquid sample through and out the intermediate detection zones of the assay device 300. The wicking zone 324 and other zones of the herein described device 300 can include a porous material such as nitrocellulose, or alternatively is a non-porous structure defined by projections as described previously. Though not shown, a hydrophilic foil cover can also be adhered or otherwise attached onto the absorbing zone 324 or the wicking zone 314 can further include non-capillary fluid driving means, such as an evaporative heater or a pump. Further details of wicking zones as used in lateral flow assay devices according to the present invention are found in patent publications US 2005/0042766 and US 2006/0239859, both of which are incorporated herein by reference in their entireties.

In this device version, the entirety of the fluid flow path of the assay device 300 including the sample addition zone 308, the reaction zones 312, 313, and the wicking zone 324 is defined by projections substantially vertical in relation to the substrate 304, and having a height, diameter and reciprocal spacing capable of creating lateral capillary flow of the sample spontaneously along the fluid flow path.

The defined flow path of the lateral flow assay devices described herein, including the device 300, can include open or closed paths, grooves, and capillaries. Preferably, the flow path comprises a lateral flow path of adjacent projections, having a size, shape and mutual spacing such that capillary flow is sustained through the flow path. In one embodiment, the flow path is in a channel within the substrate 304 having a bottom surface and side walls. In this embodiment, the projections protrude from the bottom surface of the flow channel. The side walls may or may not contribute to the capillary action of the liquid. If the sidewalls do not contribute to the capillary action of the liquid, then a gap can be provided between the outermost projections and the sidewalls to keep the liquid contained in the flow path defined by the projections. Preferably, the reagent that is used in the reaction zones 312, 313 and the capture members or detection agent used in the detection zone is bound directly to the exterior surface of the projections used in the herein described assay device 300.

Tests (assays) are typically completed when the last of the conjugate material has moved into the wicking area 324 of the lateral flow assay device 300. At this stage, a detection instrument, such as a fluorimeter or similar device, is used to scan the at least one detection zone, the detection instrument being movable and aligned optically with the flow channel 317 along an axis 319. The detection instrument that can be used to perform the various methods and techniques described herein can assume a varied number of forms. For example and as described according to the present embodiment, the instrument can be a scanning apparatus that is capable of detecting fluorescence or fluorescent signals. Alternatively, an imaging apparatus and image analysis can also be used to determine, for example, the presence and position of at least one fluorescent fluid front of an assay device. According to yet another alternative version, infrared (IR) sensors could also be utilized to track the position of fluid position in the lateral flow assay device. For instance, an IR sensor could be used to sense the ~1200 nanometer peak that is typically associated with water in the fluid sample to verify that sample had indeed touched off onto the substrate of the assay device. It should be readily apparent that other suitable approaches and apparatus capable of performing these techniques could be utilized herein.

For purposes of this embodiment, the detection instrument is incorporated within a portable (hand-held or bench top) testing apparatus that includes means for receiving at least one lateral flow assay device 300 and defining a scan path along the flow channel 317 and coincident with axis 319 relative to a light emitting element of the detection instrument, such as a laser diode and an optical system and filtering, having an optical axis and capable of providing quantitative measurement of fluorescent signal at predefined wavelengths as emitted from the assay fluorophores in the lateral flow assay device, and as discussed herein. Other devices or testing apparatus can also be used to retain a detection instrument for purposes of the herein described monitoring methods. For example, a mainframe clinical analyzer can be used to retain a plurality of lateral flow assay devices as described in U.S. Patent Application Publication No. 2013/0330713, the entire contents of which are herein incorporated by reference. In a clinical analyzer, at least one detection instrument such as a fluorimeter can be aligned with the flow channel 317 of the assay device 300 and provided, for example, in relation to an incubator assembly as a monitoring station in which results can be transmitted to a contained processor.

One exemplary flow monitoring methodology is now herein described. For purposes of this method and in the description that follows, a lateral flow assay device as previously described according to FIG. 4 is utilized, although other device configurations could be utilized, this embodiment intended to be exemplary of a more generic technique.

For purposes of this particular version, a pair of detection or reader apparatuses could be employed; namely, a first reader apparatus 331 that is linearly aligned with the linear section of the flow channel 317 containing at least one detection zone along axis 319 and a second reader apparatus 334 that is linearly aligned with the wicking zone 324 along a second axis 337. In each of the foregoing apparatus, a reader or detector such as fluorimeter can be translated along the respective axes 319, 337 relative to specific areas designated on the lateral flow assay device 300. Alternatively, a single reader apparatus (not shown) could be utilized, the reader apparatus having capability of translating longitudinally and laterally so as to selectively align with either detection axis 319 or 337.

Before sample is administered or otherwise dispensed, the lateral flow assay device 300 can first be assessed by performing a so-called "dry scan" or read using each of the first and second reader apparatus 331, 334 at specific areas of the lateral flow assay device 300. For purposes of this embodiment, readings are taken using the second reader apparatus 334 adjacent the entrance and exit of the wicking zone 324 at designated positions 351 and 355, respectively, and the first reader apparatus 331 takes a reading at the at least one detection zone. The purpose of the "dry scan" is to obtain a background signal level prior to dispensing sample and comparing the background signal to a known standard. Readings that exceed the background standard can be indicative of error conditions, such as device structural flaws or a premature leakage of reagent or previous use. In any event, determinations that are not within a suitable range of the background signal can be detected by either reader apparatus and cause the assay device 300 to be discarded.

Alternatively, or in addition to, immediately upon installation of the device into the testing apparatus and either before or after addition of sample to the device 300, readings are taken at the wicking zone, such as at the exit of the wicking zone 324, at a designated position 355. Readings that exceed the background standard can be indicative of error conditions, such as premature leakage of reagent or evidence of previous use. In any event, determinations that are not within a suitable range of the background signal can be detected and cause the assay device 300 to be discarded. More specific details relating to the foregoing assay device 300 are provided in U.S. Patent Application Publication No. 2014/0141527 A1, entitled: Quality Process Control Of A Lateral Flow Assay Device Based On Flow Monitoring, the entire contents of which is herein incorporated by reference.

There is a general and ongoing need in the field to improve the flow characteristics of lateral flow assay devices, such as those previously described. For example, the amount of sample which is applied to the devices of FIGS. 2-4 is typically of the order of about 10 to 200 microliters, wherein a considerable amount of this sample is wasted. It is a general goal in the field to minimize the quantity of sample required to apply in order to adequately perform a test, but without sacrificing accuracy or reliability of results obtained. In addition and in the case of the lateral flow assay device shown in FIG. 4, the dual reagent areas or zones merge via separate paths into the flow channel. There is a need for such devices and others to insure adequate mixing has occurred between an applied sample and reagent prior to detection. Still further, it has been determined that the configuration of projections that creates a suitable amount of capillary force for moving sample through the device along a defined fluid flow path additionally creates a preferred distribution pattern in regard to an applied detection material. It would be advantageous to utilize this configuration in order to preferably and repeatably retain the deposited detection material in a defined area and also to more uniformly dissolve the deposited material when contacted with moving sample. Still further and with a need to use reduced amounts of sample, the time required to produce an assay result can be insufficient for certain markers, meaning additional time may be required for the fluidic sample to completely fill the absorbing zone which can be important, for example, for purposes of conducting test measurements for an analyte of interest. As discussed herein, the use of a hydrophilic cover improves the wicking ability of sample through the assay device. The edge of this cover, however, induces effects that are contrary to performance of the assay device. To that end, features are further required to hinder these effects and thereby improve reliability.

BRIEF DESCRIPTION

Therefore and according to one aspect, there is provided a lateral flow assay device comprising:

a non-porous substrate having a top surface;

a sample addition area including a cover having an aperture and a filter peripherally supported within the aperture configured for adding a sample fluid, the cover being disposed above the substrate and defining a spacing therebetween, the supported filter including a portion in direct contact with the top surface of the substrate and creating a peripheral reservoir of sample fluid that passes through the filter, said peripheral reservoir being retained by capillary forces between the filter and the substrate that retains a volume of fluid sample; and a sample receiving zone extending along a portion of the substrate and into contact with only a portion of the peripheral reservoir, the sample receiving zone being configured to create capillary pressure for drawing fluid from the peripheral reservoir but without disturbing the integrity of the reservoir.

In at least one version, the sample receiving zone is disposed along a fluid flow path of the assay device, wherein the assay device further includes at least one reagent zone and an absorbing zone, each disposed along the fluid flow path.

In at least one version, the sample receiving zone is defined by a plurality of projections extending from the top surface of the substrate, the plurality of projections having a reciprocal spacing and dimensions that create lateral capillary flow relative to the peripheral reservoir.

According to at least one embodiment, the filter includes a surface section extending between the portion directly contacting the substrate and a supporting edge of the cover aperture, the surface section forming an angle $\alpha$ with the top surface of the substrate. The angle $\alpha$ is greater than zero and preferably is about 10 degrees.

In at least one version of the device, a plurality of sample receiving zones can interconnect with separate portions of the peripheral reservoir and extend in different planar directions therefrom.

The lateral flow assay device further comprises a flow channel interconnecting the reagent zone, the detection zone and the absorbing zone and in which the sample receiving zone is appreciably smaller in size than prior art assay devices. The sizing of the sample receiving area can include a width dimension that is as wide as that of the flow channel. According to one preferred version, the width dimension of the sample receiving zone is between about one and three times the width dimension of the flow channel and more preferably about two times the width dimension of the flow channel.

According to another aspect, there is provided a method for reducing the amount of fluid required to conduct an assay using a lateral flow assay device, the method comprising:

providing a sample addition zone relative to the device, the sample addition zone including a cover having an aperture and a filter peripherally supported by the aperture, the filter having at least one portion in direct contact with a substrate of the assay device;

creating a peripheral reservoir bounded by the top surface of the substrate, a bottom surface of the filter and an angle subtended between the substrate and the filter;

creating at least one sample receiving area of a lateral flow assay device in contact with a only a portion of the peripheral reservoir; and drawing sample from the peripheral reservoir into the at least one sample receiving area without disturbing the integrity of the peripheral reservoir.

In one version, the method further comprises sizing the at least one sample receiving area relative to a flow channel of the assay device interconnecting at least one reagent zone and an absorbing zone along a fluid flow path of the device. In a preferred version, the sample receiving area is sized to have a width dimension that is comparably sized to that of the width dimension of the flow channel. In at least one embodiment, the width of the at least one sample receiving area is about 1-3 times the width dimension of the flow channel and more preferably about two times the width dimension of the flow channel.

According to yet another aspect, there is provided a lateral flow assay device comprising:

a substrate;

a sample receiving zone disposed on a surface of the substrate; and at least one reagent zone disposed downstream of the sample receiving zone along at least one defined fluid flow path, the at least one reagent zone and the sample receiving zone comprising a plurality of projections extending upwardly from the upper surface of the substrate, the plurality of projections having dimensions and spacing between the microposts that enable capillary flow of an applied fluid, the at least one reagent zone including a portion having deposited thereto a quantity of a detection material that produces a visually detectable signal when wetted by a sample, and in which the detection material portion is defined by a substantially hexagonal configuration having cut forming edges about the periphery thereof, the cut forming edges being configured for causing a sample flowing from the sample receiving zone to uniformly dissolve the applied detection material.

According to at least one version, the detection material is deposited onto the projections in liquid form and is caused to form the substantially hexagonal configuration based on the configuration and spacing of the projections and in which the cut forming edges are disposed about a hexagonally shaped area of the reagent area.

In at least one embodiment, the cut forming edges cut neighboring projections at a maximum at the midpoint of each side of the hexagonal configuration and do not cut any projections at the corners or vertices of the configuration.

According to yet another aspect, there is provided a method for enabling uniform dissolution of a deposited detection material relative to a flowing sample on a lateral flow assay device, the assay device having a sample receiving zone fluidically connected to at least one reagent zone along a fluid flow path, each of the sample receiving zone and at least one reagent zone having a plurality of projections having dimensions and a reciprocal spacing therebetween that promotes lateral capillary pressure upon an applied sample along the fluid flow path and in which a detection material is deposited onto an areal portion of the reagent area, the projections being configured to create a substantially hexagonal configuration of a deposited detection material based on the arrangement of the projections, the method comprising:

cutting a portion of the projections along edges of the substantially hexagonal configuration in order to promote flow of sample to the deposited detection material to promote uniform dissolution; and depositing the detection material onto the substantially hexagonal configuration such that the deposited detection material is retained within the substantially hexagonal configuration.

In at least one version, the projections are cylindrical in configuration and in which the edge cuts made to the hexagonal surfaces are a maximum at the center of the span between corners of the configuration and in which no cuts are made at the corners of the hexagonal configuration.

According to yet another aspect, there is provided a lateral flow device comprising:

a substrate having an upper surface;

a sample receiving zone;

at least one reagent zone disposed downstream relative to the sample receiving zone along a defined fluid flow path, the at least one reagent zone including a reagent material that produces a detectable signal when contacted by a fluidic sample;

at least one detection zone disposed downstream of the at least one reagent zone along the defined fluid flow path; and a flow channel interconnecting the at least one reagent zone and the at least one detection zone along the defined fluid flow path, the flow channel having a plurality of projections extending from the upper surface of the substrate, the projections being dimensioned with heights and diameters and having a center to center reciprocal spacing that induce lateral capillary flow and in which a portion of the flow channel is defined by a serpentine configuration between an entrance region and an exit region and an intermediate mixing region, the projections in the flow channel being disposed in a series of rows spaced from one another in parallel relation along a first direction and the rows extending in a second direction that is transverse to the first direction and wherein the spacing between adjacent rows in the first direction is greater than the spacing between projections in each row in the mixing region to promote mixing of the fluidic sample with at least one reagent.

Within the mixing region, the serpentine flow channel can be defined with rows having a greater number of projections extending in the second direction as compared to those in the entrance and exit portions sufficiently to induce fluidic movement or wetting between rows of projections in the second planar direction prior to advancing to a subsequent row. In one version, the number of projections in the entrance and exit portions can total between 6-8 projections while the number of projections in the mixing region can increase to a maximum of about 20 projections in the center of the mixing region or a ratio of about 3:1.

According to yet another aspect, there is provided a method to promote mixing of sample and at least one reagent in a lateral flow assay device, the assay device comprising a sample addition zone and at least one reagent zone and an absorbing zone disposed along at least one fluid flow path, said method comprising:

providing a flow channel between a detection zone of the device and the at least one reagent zone, the flow channel having a plurality of projections configured to induce lateral capillary flow of an applied sample, the projections being arranged in parallel rows spaced by one another along a first direction and the rows extending in a second direction transverse to the first direction, configuring the flow channel with a serpentine mixing zone in which the number of projections in each spaced row increases to a maximum in the center of the mixing zone and is equal to that of the remainder of the flow channel at the entrance and exit of the mixing zone such that the arrangement of the projections promotes flow in both the first and second directions to promote mixing of sample and reagent.

According to yet another aspect, there is provided a lateral flow assay device comprising:

a substrate having a surface;

a sample addition zone at a first end of a defined fluid flow path;

an absorbing or wicking zone disposed at an opposite end of the fluid flow path, the sample addition zone and the absorbing zone having a plurality of projections extending from the substrate surface that are configured to enable capillary flow of an introduced fluid along the fluid flow path; and at least one feature configured to delay the overall flow rate of fluid entering the absorbing zone.

The at least one feature can comprise a serpentine array of the projections, the array being coextensive with a flow channel of the assay device interconnecting the sample receiving zone and the absorbing zone, the serpentine array being defined by a plurality of segments extending in a back and forth direction which is transverse to the direction of the flow channel. Preferably, the array is disposed within the absorbing zone.

According to yet another aspect, there is provided a lateral flow device comprising:

a substrate having a surface;

a sample addition zone at a first end of a defined fluid flow path;

an absorbing zone disposed at an opposite end of the fluid flow path, the sample addition zone and the absorbing zone having a plurality of projections extending from the substrate surface that are configured to enable capillary flow of an introduced fluid along the fluid flow path;

a hydrophilic foil or tape cover disposed over the projections of the absorbing zone, said cover having a peripheral edge extending across the entrance of the absorbing zone across a flow channel entering the absorbing zone; and at least one feature that increases the flowability of fluid into the absorbing zone across the peripheral edge of the hydrophilic foil or tape.

In at least one embodiment, the at least one feature comprises at least one of a groove or a bar formed in the substrate in a direction that is parallel to the direction of flow of the fluid and extending perpendicular and across the outer edge of the cover.

According to at least one other version, at least one feature is further configured to prevent wicking of fluid along the outer edge of the hydrophilic cover. The at least one feature to prevent wicking can comprise at least one groove disposed transverse to the outer edge of the hydrophilic tape or foil cover and extending across either side of the edge. Alternatively, a plurality of the grooves can be disposed about at least a portion of the periphery of the hydrophilic cover.

According to yet another embodiment, a lateral flow assay device comprises:

a substrate having a surface;

a sample addition zone at a first end of a defined fluid flow path;

an absorbing zone disposed at an opposite end of the fluid flow path, the sample addition zone and the absorbing zone having a plurality of projections extending from the substrate surface that are configured to enable capillary flow of an introduced fluid along the fluid flow path;

a hydrophilic tape or foil cover disposed onto the absorbing zone, the cover having a peripheral outer edge; and at least one feature for minimizing the lateral wicking effects of the outer peripheral edge of the cover to an incoming fluid.

According to at least one embodiment, the at least one wicking negating feature comprises at least one groove disposed in the surface of the substrate, the at least one groove extending in a direction that is substantially transverse to the outer edge of the hydrophilic tape or foil cover and extending to opposite sides thereof. Alternatively, a plurality of grooves can be disposed about the periphery of the hydrophilic foil or tape cover, including disposing a plurality of the grooves disposed in relation to the periphery of the outer edge, wherein at least a pair of the grooves can be disposed adjacent the flow channel of the device.

In at least one version, a plurality of fluid paths can extend outwardly from the sample receiving area in various directions and in which the fluid paths can be constructed such that various flow properties can be individually adjusted or tailored for specific analytes and the like.

In at least one other version, at least one fluid path(s) extending from the sample receiving area is defined by a plurality of projections having a reciprocal spacing and dimensions that create lateral capillary flow upon application of a sample.

One advantage provided is that of less potentially wasted sample, meaning that smaller sample volumes can be used as compared to prior known lateral flow assay devices.

Another advantage provided is that the above-noted features can be incorporated using known manufacture processes and materials.

Another advantage is that easier conjugate disposition and more consistent deposition shape, thereby reducing waste in manufacture, quicker wetting and dissolution of the deposited conjugate, reducing of sample pre-binding in the detection zone and reducing variabilities in conjugate wetting.

Yet another advantage is that of better mixing of the conjugate with sample, reducing variability between tests.

Still another advantage is that fluid flow time is adjustable to a longer time using the flow restrictor to allow for increased sensitivity, improved precision and better wash with less sample volume.

Yet another advantage realized is that of more robust flow and reduced flow stoppage at the edge of the hydrophilic tape cover. In addition, there is a reduced chance of fluid wicking along the edge of the tape cover and a reduced chance of contamination and flow variability.

These and other features and advantages will be readily apparent from the following Detailed Description, which should be read in conjunction with the accompanying drawings.

DETAILED DESCRIPTION

Figure 1:
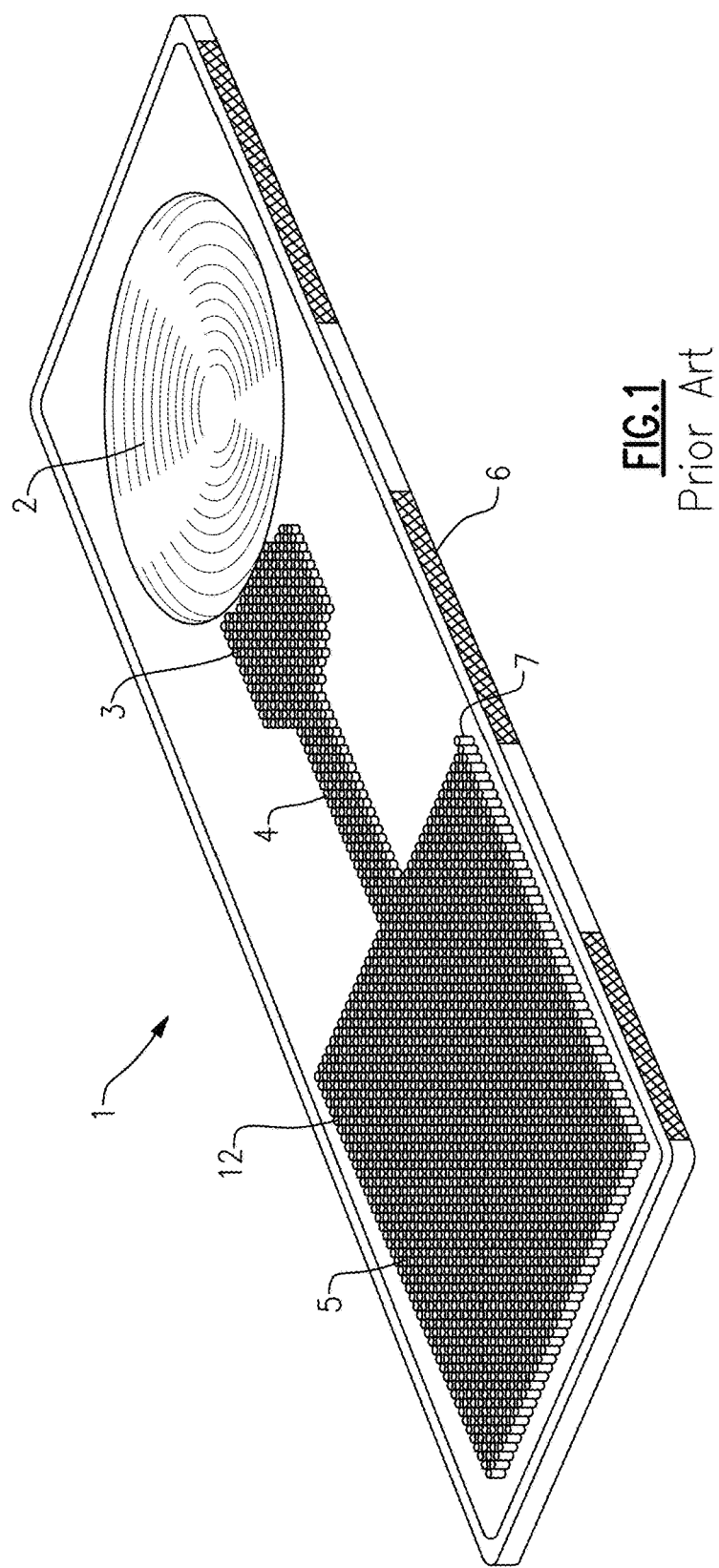
FIG. 1 is a top perspective view of a known lateral flow assay device.
Figure 2:
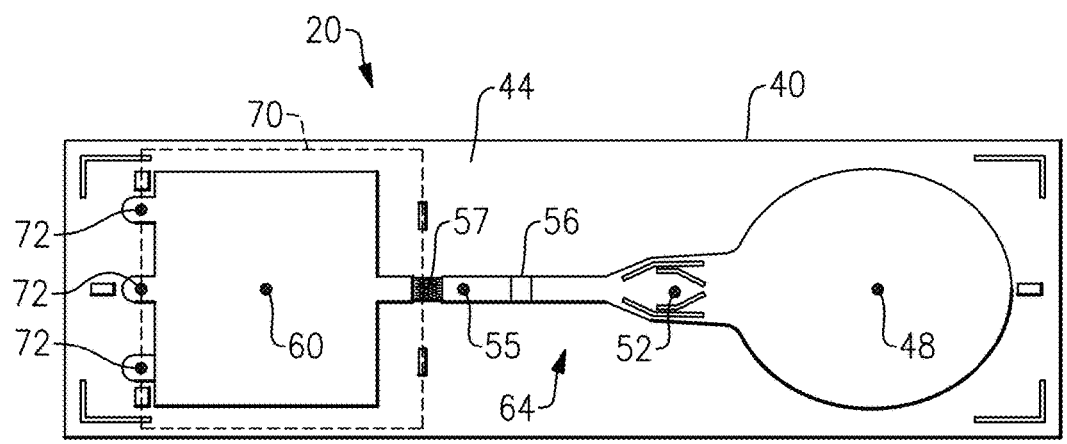
FIG. 2 is a top plan view of another known lateral flow assay device.
Figure 3:
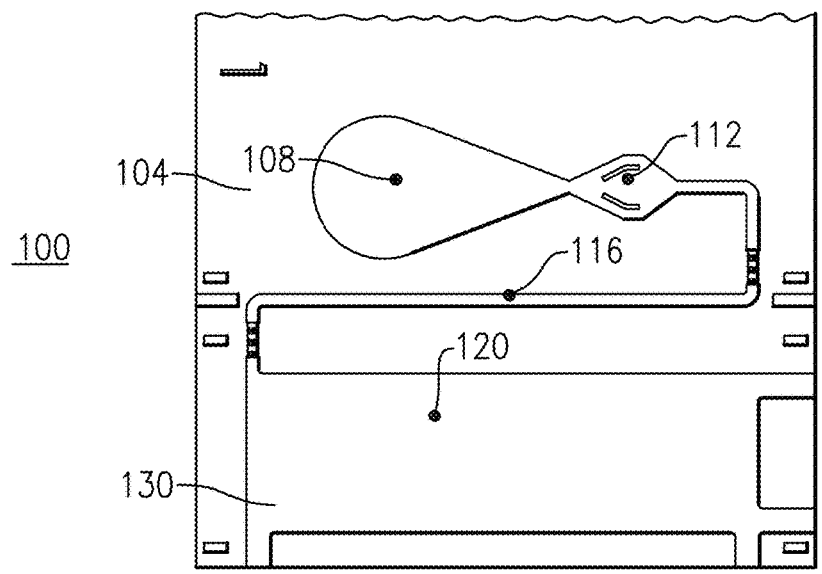
FIG. 3 is a top plan view of yet another known lateral flow device.

The following discussion relates to certain exemplary embodiments of a lateral flow assay device having improved features for promoting flow characteristics of an applied sample. Throughout the course of this discussion, several terms are used in order to provide an adequate frame of reference with regard to the accompanying drawings. These terms, which can include "top", "upper", "lower", "bottom" and the like are not intended to limit the overall scope of the inventive concepts described herein.

In addition, the drawings are intended to convey the salient features of the depicted assay device. To that end, the drawings are not necessarily to scale and should not be overly relied upon by the reader.

As used in this application, including the claims, the singular forms "a", "an" and "the" are intended to include plural referents unless the context clearly indicates otherwise.

The term "about" as used in this specification is used in connection with a numerical value to denote a level of accuracy, which is familiar and acceptable to a person skilled in the art. The interval governing this term is preferably ±30%.

In terms of defining certain of the terms that follow, the term "analyte" is used as a synonym of the term "marker" and intended to minimally encompass any chemical or biological substance that is measured quantitatively or qualitatively and can include small molecules, proteins, antibodies, DNA, RNA, nucleic acids, virus components or intact viruses, bacteria components or intact bacteria, cellular components or intact cells and complexes and derivatives thereof.

The term "sample" as used herein refers to a volume of a liquid, solution or suspension, intended to be subjected to qualitative or quantitative determination of any of its properties, such as the presence or absence of a component, the concentration of a component, etc. Typical samples in the context of this application as described herein can include human or animal bodily fluids such as blood, plasma, serum, lymph, urine, saliva, semen, amniotic fluid, gastric fluid, phlegm, sputum, mucus, tears, stool, etc. Other types of samples are derived from human or animal tissue samples where the sample tissue has been processed into a liquid, solution or suspension to reveal particular tissue components for examination. The embodiments of the present application, as intended, are applicable to all bodily samples, but preferably to samples of whole blood, urine or sputum.

In other instances, the sample can be related to food testing, environmental testing, bio-threat or bio-hazard testing, etc. The foregoing, however, represents only a small example of samples that can be used for purposes of the present invention.

In the present invention, any determinations based on lateral flow of a sample and the interaction of components present in the sample with reagents present in the device or added to the device during the procedure and detection of such interaction, either quantitatively or qualitatively, may be for any purpose, such as diagnostic purposes. Such tests are often referred to as "lateral flow assays".

Examples of diagnostic determinations include, but are not limited to, the determination of analytes, also referred to synonymously as "markers", specific for different disorders, e.g., chronic metabolic disorders, such as blood glucose, blood ketones, urine glucose, (diabetes), blood cholesterol, (atherosclerosis, obesity, etc); markers of other specific diseases, e.g., acute diseases, such as coronary infarct markers (e.g., tropinin-T, NT-ProBNP), markers of thyroid function (e.g., determination of thyroid stimulating hormone (TSH)), markers of viral infections (the use of lateral flow immunoassays for the detection of specific viral antibodies), etc.

Yet another important field is the field of companion diagnostics in which a therapeutic agent, such as a drug, is administered to an individual in need of such a drug. An appropriate assay is then conducted to determine the level of an appropriate marker to determine whether the drug is having its desired effect. Alternatively, the assay device usable with the present invention can be used prior to the administration of a therapeutic agent to determine if the agent will help the individual in need.

Yet another important field is that of drug tests, for easy and rapid detection of drugs and drug metabolites indicating drug abuse; such as the determination of specific drugs and drug metabolites in a urine or other sample.

The term "lateral flow device" as discussed throughout this application herein refers to any device that receives a fluid, such as sample, and includes a laterally disposed fluid transport or fluid flow path along which various stations or sites (zones) are provided for supporting various reagents, filters, and the like through which sample traverses under the influence of capillary or other applied forces and in which lateral flow assays are conducted for the detection of at least one analyte (marker) of interest.

The terms "automated clinical analyzer", "clinical diagnostic apparatus", or "clinical analyzer" as discussed herein, refer to any apparatus enabling the scheduling and processing of various analytical test elements, including lateral flow assay devices, as discussed herein and in which a plurality of test elements can be initially loaded for processing. This apparatus further includes a plurality of components/systems configured for loading, incubating and testing/evaluating a plurality of analytical test elements in automated or semi-automated fashion and in which test elements are automatically dispensed from at least one contained storage supply, such as a cartridge or other apparatus, without user intervention.

The term "testing apparatus" as used herein refers to any device or analytical system that enables the support, scheduling and processing of lateral flow assay devices. A testing apparatus can include an automated clinical analyzer or clinical diagnostic apparatus such as a bench, table-top or main frame clinical analyzer, as well as point of care (POC) and other suitable devices. For purposes of this definition, the testing apparatus may include a plurality of components/systems for loading and testing/evaluating of at least one lateral flow device, including detection instruments for detecting the presence of at least one detectable signal of the assay device.

The terms "zone", "area" and "site" as used throughout this application, including the claims define parts of the fluid flow path on a substrate, either in prior art devices or in at least one lateral flow assay device according to an embodiment of this invention.

The terms "reaction" is used to define any reaction, which takes place between components of a sample and at least one reagent or reagents on or in the substrate, or between two or more components present in the sample. The term "reaction" is in particular used to define the reaction, taking place between an analyte (marker) and a reagent as part of the qualitative or quantitative determination of the analyte.

The terms "substrate" or "support", as used herein, refers to the carrier or matrix to which a sample is added, and on or in which the determination is performed, or where the reaction between analyte and reagent takes place.

The term "detection" and "detection signal" as used herein, refers to the ability to provide a perceivable indicator that can be monitored either visually and/or by machine vision, such as a detection instrument.

The term "process-related event" refers herein to an event that occurs prior to the detection of analyte in a lateral flow assay device, such as, for example, the addition of at least one reagent, such as a wash reagent.

Components of the herein described lateral flow assay devices (i.e., a physical structure of the device whether or not a discrete piece from other parts of the device) described herein can be prepared from copolymers, blends, laminates, metallized foils, metallized films or metals. Alternatively, device components can be prepared from copolymers, blends, laminates, metallized foils, metallized films or metals deposited one of the following materials: polyolefins, polyesters, styrene containing polymers, polycarbonate, acrylic polymers, chlorine containing polymers, acetal homopolymers and copolymers, cellulosics and their esters, cellulose nitrate, fluorine containing polymers, polyamides, polyimides, polymethylmethacrylates, sulfur containing polymers, polyurethanes, silicone containing polymers, glass, and ceramic materials. Alternatively, components of the device can be made with a plastic, elastomer, latex, silicon chip, or metal; the elastomer can comprise polyethylene, polypropylene, polystyrene, polyacrylates, silicon elastomers, or latex. Alternatively, components of the device can be prepared from latex, polystyrene latex or hydrophobic polymers; the hydrophobic polymer can comprise polypropylene, polyethylene, or polyester. Alternatively, components of the device can comprise TEFLON®, polystyrene, polyacrylate, or polycarbonate. Alternatively, device components are made from plastics which are capable of being embossed, milled or injection molded or from surfaces of copper, silver and gold films upon which may be adsorbed various long chain alkanethiols. The structures of plastic which are capable of being milled or injection molded can comprise a polystyrene, a polycarbonate, or a polyacrylate. In a particularly preferred embodiment, the lateral flow assay devices are injection molded from a cyclo olefin polymer, such as those sold under the name Zeonor®. Preferred injection molding techniques are described in U.S. Pat. Nos. 6,372,542, 6,733,682, 6,811,736, 6,884,370, and 6,733,682, all of which are incorporated herein by reference in their entireties.

Figure 5:
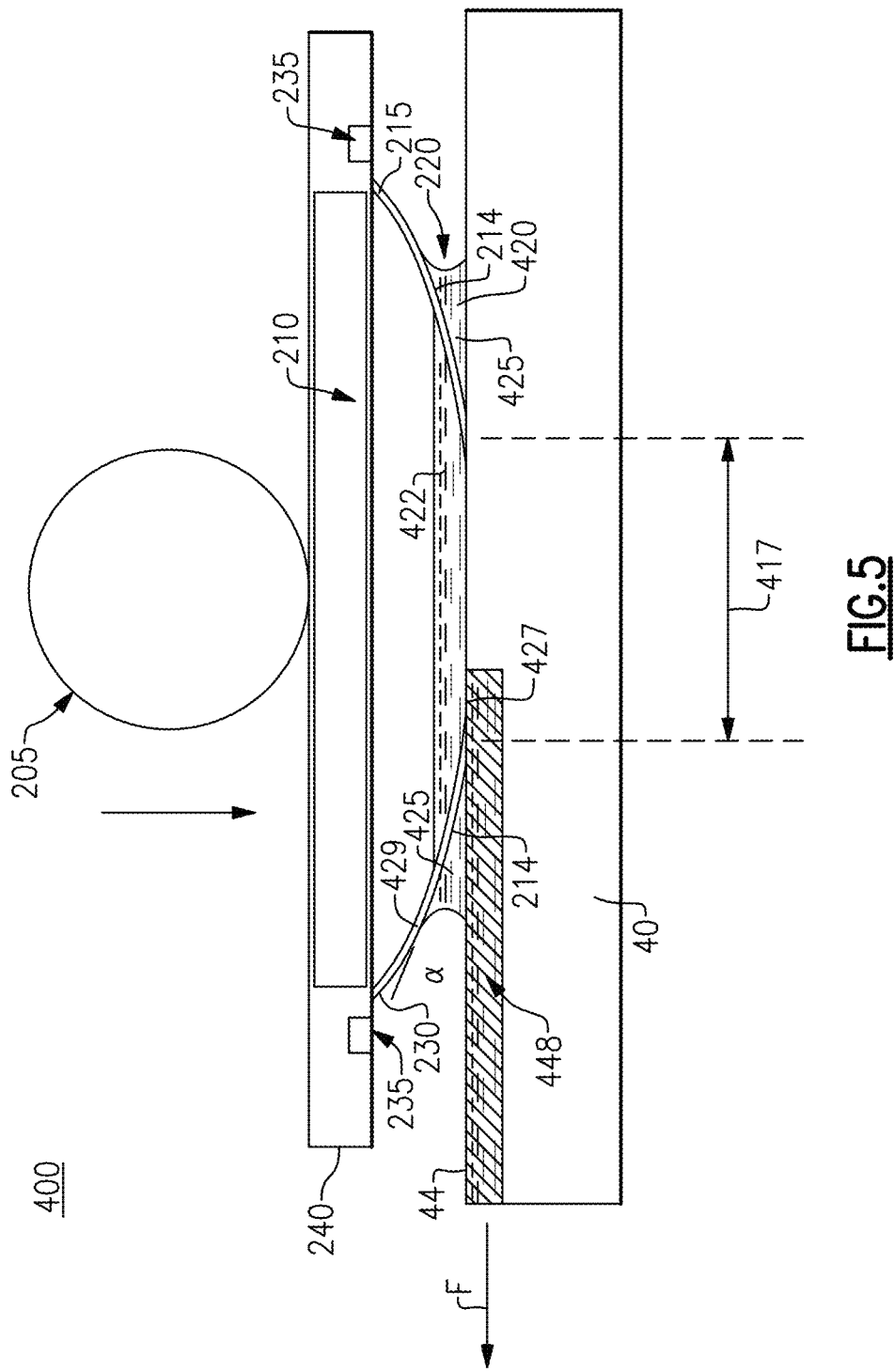
FIG. 5 is a side elevational view of a sample addition and sample receiving zone of a lateral flow assay device made in accordance with an exemplary embodiment.
Figure 7:
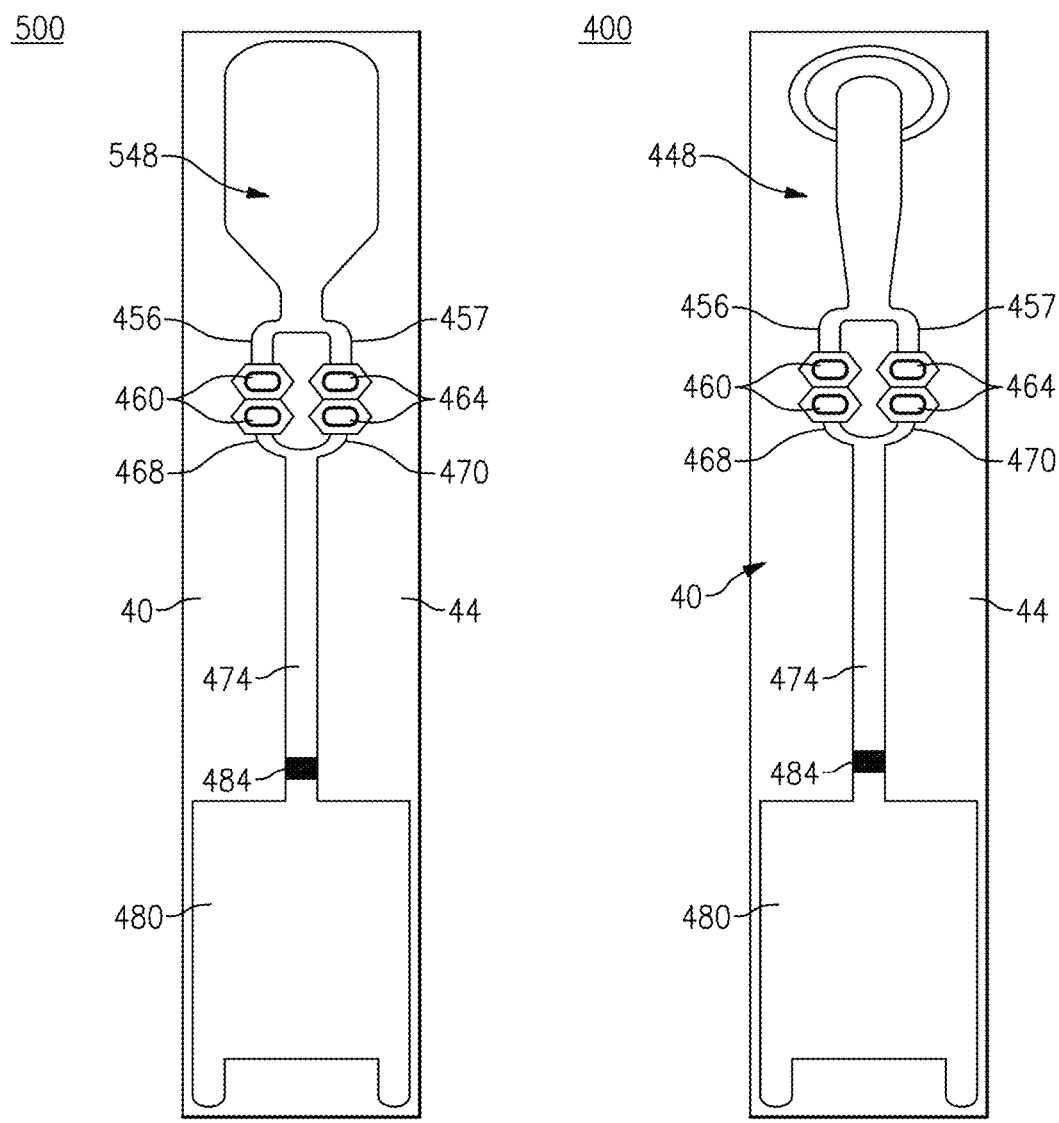
FIG. 7 is a comparative top plan view between a lateral flow assay device with a known sample receiving zone and a lateral flow assay device having a sample receiving zone in accordance with an exemplary embodiment.

Referring to FIGS. 5 and 7, there is shown a lateral flow assay device 400 made in accordance with an exemplary embodiment. The assay device 400 comprises a planar substrate 40 made from a non-porous (i.e., non-fluid permeable) material, such as a moldable plastic, having a sample receiving zone 448 that forms a part of a defined or created fluid flow path and in which the assay device 400 further includes multiple reagent zones 460, 464 disposed in parallel relation based on flow channels 456, 457 that split or divide from the sample receiving zone 448 and then merge or splice the reagent zones 460, 464 via respective flow channels 468, 470 into a single narrowed flow channel 474. The single narrowed channel 474 further extends into an absorbing zone 480, the flow channel 474 having at least one detection zone 484. Each of the disposed zones include flow control elements that enable fluid to be moved along the defined fluid flow path. According to this embodiment, a plurality of projections 490 extend upwardly from the upper surface 44 of the substrate 40, the projections 490 being configured dimensionally and in terms of their relative spacing to induce lateral capillary flow beginning at the sample receiving zone 448.

Referring specifically to FIG. 5, a filtrate 420 flows under capillary action away from the sample receiving zone 448 (e.g., in direction F). A cover or lid 240 is arranged over the substrate 40 and includes an aperture 210, defining a receiving port that is configured to receive the sample 205. For purposes of clarity, the cover 240 is not shown in FIG. 7.

A filter 215, having a substantially concave shape according to this embodiment is supported peripherally within the aperture 210 of the cover 240 and configured to permit at least a portion of the sample 205 to pass through the filter 215 as a filtrate 420. The filter 215 can be supported around its entire perimeter by the cover 240, or the filter 215 can have some portions of its perimeter supported by the cover 240 with other portions not supported. The portion of the sample 205 that does not pass through the filter 215 is herein referred to as the residue 422 (e.g., red blood cells in the case of whole blood being used as a sample). The supported filter 215 includes at least one contact portion 417 in direct contact with the substrate 40 to create a contact area 427 that at least partly overlaps the sample addition zone 448. The filter 215 also includes an adjacent portion 429 that extends from the at least one contact portion 427 to the supported edge 230 (periphery) of the filter 215 to define with the substrate 40, a peripheral reservoir 425 that is configured to support and retain a volumetric quantity of the filtrate 420. For purposes described herein, the filter 215 can be circular. Alternatively, the filter 215 could also assume other configurations, such as elliptical or polygonal (square, rectangular, etc).

The formation of the peripheral reservoir 425 is now briefly described. When a quantity of the fluid sample 205 (e.g., whole blood) is dispensed onto the filter 215, the filtrate 420 beneath the filter 215 contacts two (2) surfaces, namely, the bottom side or surface 214 of the filter 215 and the top surface 44 of the planar substrate 40. Each of the these surfaces 44, 214 are hydrophilic and as a result, the filtrate 420 wets each surface 44, 214, forming a meniscus 220. The meniscus 220, the filter surface 214 and the top surface 44 of the substrate 40 bound the peripheral reservoir 425.

The peripheral reservoir 425 is configured to retain the filtrate 420 by means of capillary pressure developed between the substrate 40 and the extending portion 429 of the filter 215. The capillary pressure exerted by the flow control elements (e.g., the projections 490, FIG. 6) on the substrate 40 is sufficiently large to locally overcome the capillary pressure maintaining the peripheral meniscus 220 that retains the peripheral reservoir 425. This differential causes the volumetric fluid to be drawn from the peripheral reservoir 425 wherein the flow rate of the assay device 400 (out of the peripheral reservoir 425) is slower than that of the filtrate flow rate into the formed reservoir 425. In an example, substantially all of the filtrate 420 passes from the sample 205 into the peripheral reservoir 425 in about one (1) minute, but at least some of the filtrate 420 is retained within the peripheral reservoir 425 for about ten (10) minutes during the conduction of the assay.

Dynamically and if the inflow rate (i.e. filtration rate at which filtrate 420 passes through the filter 215) is higher than the outflow rate (i.e., the flow rate of the filtrate from the peripheral reservoir 425 to the sample receiving zone 448), the perimeter and the volume of the reservoir 425 will increase. In cases in which the meniscus 220 reaches the supported peripheral edge 230 of the filter 215 and the underside of the cover 240, which may include various obstructions, such as a welding groove 235, amounts of sample fluid (filtrate 420) may then become trapped or pinned. The creation of trapped fluid can lead to a shortage of sample flowing to and filling the wicking zone 480 of the assay device 400, which is undesirable especially when using smaller sample volumes (e.g., microsamples of 50 microliters or less). As a result, less filtrate 420 (e.g., plasma) will be available to flow downstream in the assay device 400 along the fluid flow path toward the reagent zones 460, 464, the detection zone(s) 484 and the wicking zone 480. Moreover, the preceding effect can further stop or impede flow within the fluid flow path, or cause flow to occur very slowly due to lack of fluid sample in the peripheral reservoir 425.

For whole blood filtration, the meniscus 220 between the filter 215 and the assay device 400 grows initially when the pores of the filter 215 are relatively open and the hematocrit level of the sample is still close to a normal range. In the later phases of filtration, however, most of the pores of the filter 215 become clogged by the presence and accumulation of the filtered red blood cells, and the hematocrit level in the residue 422 increases as a result of losing plasma to the other side of the filter 215. As a result, inflow into the peripheral reservoir 425 from filtration becoming slower than outflow from the reservoir 425 to the sample receiving zone 448, and the meniscus 220 and volume in the peripheral reservoir 425 are caused to shrink.

The peripheral reservoir 425, with the meniscus 220 as a movable sidewall thereof, permits fast filtration and much slower, but desirable channel flow. In an example, a flow rate of about 0.5 to 2.0 µL/minute in the device along the flow path is desirable for about a 10-15 minute total assay time and sufficient reaction time for the assay to generate a sufficient signal for acceptable assay sensitivity.

As noted, the volume in the peripheral reservoir 425 of the fluid from sample 205 is determined by the size and shape of the contact area 417, the size and shape of the filter 215 and the angle α formed between the filter 215 and the top surface 44 of the substrate 40. The formation of the peripheral reservoir 425 and the sample addition zone 448, including the effects created by varying each of the contact area, filter and subtended angle are each described in greater detail in U.S. Ser. No. 14/817,946, entitled: Lateral Flow Assay Device With Filtration Flow Control, incorporated by reference in its entirety.

Figure 6:
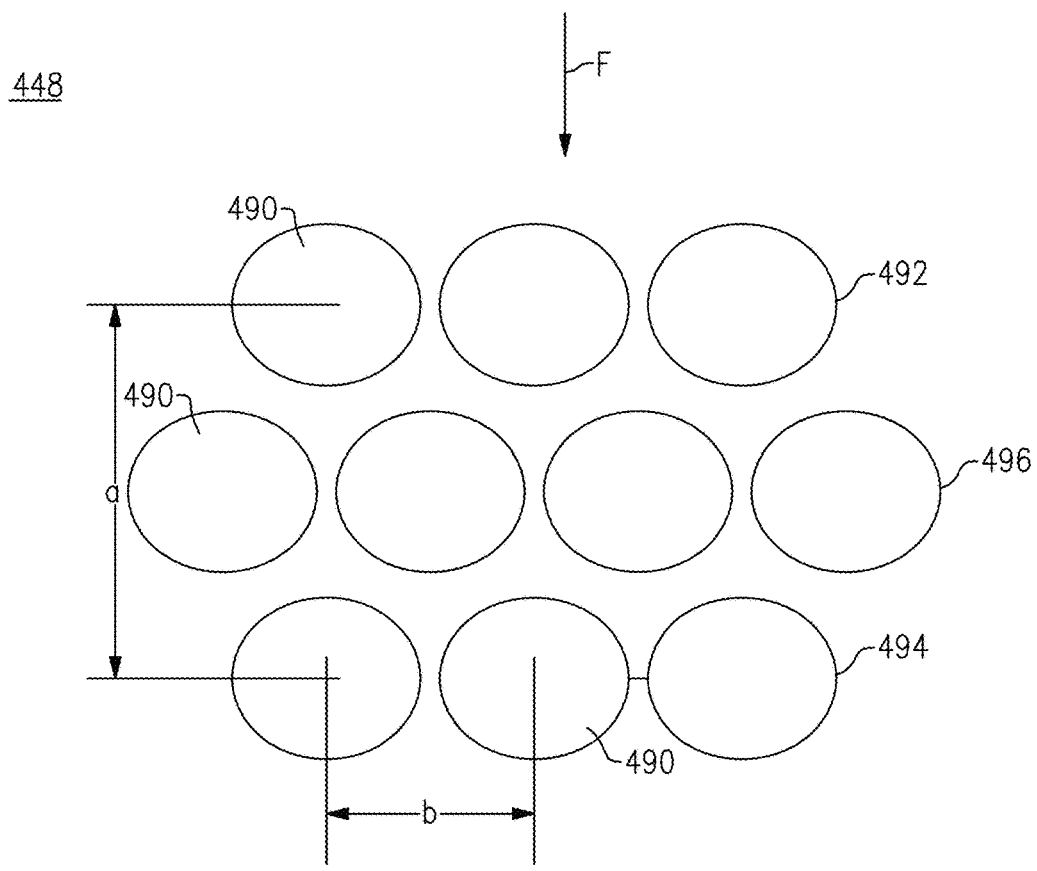
FIG. 6 is a partial top view depicting an exemplary arrangement of flow control elements for the lateral flow assay device of FIG. 5.

According to this specific device design, the projections 490 as disposed in the sample addition area 448 of the lateral flow assay device 400 are defined in a predetermined pattern, which is partially depicted with reference to FIG. 6. To facilitate capillary force in the direction F, the projections 490 are aligned in separate rows 492, 494, 496, each row being staggered relative to an adjacent row by about one half a diameter of the projections 490 and with the first and third rows 492, 494 being fully aligned with each other. The determination of whether the projections 490 are maintained in columns or rows is based on convention for purposes of this description depending on the direction of the fluid flow path in the device 400. The diameter of the projections 490 according to this exemplary embodiment vary between about 65 and 80 microns, and more preferably the diameter of each projection 490 is about 74 microns. In addition, the height of the projections 490 is preferably in the range of about 60 to 70 microns and more preferably is about 65 microns. As shown, a predetermined center to center spacing "a" is defined between the aligned rows 492, 494, while a second predetermined spacing "b" is defined between the centers of adjacent projections 490 within each individual row. According to this specific embodiment, the spacing "a" between aligned rows is about 160-170 microns and preferably about 165 microns and the spacing "b" between adjacent projections 490 is between about 80 and 90 microns and preferably about 85 microns. This arrangement and relative sizing is provided for the sample addition area of the assay device 400. A similar arrangement is provided in each of the adjacent zones along the fluid flow path of the device 400. The foregoing arrangement that includes staggering of the rows and defined reciprocal spacing between rows and columns of the projections 490 creates capillary flow that essentially pulls the sample in the direction F towards the dual reagent areas 460, 464.

The overall benefit of the peripheral reservoir 425 enables a fairly specific and considerably smaller sample receiving zone 448 to be provided for the assay device 400. Referring to FIG. 7, a similar known lateral flow assay device 500 is shown for purposes of comparison, the device 500 having each of the same features of the assay device 400, with the exception of the sample receiving zone. For the sake of clarity, the same reference numerals are used to label similar components. More specifically and with reference to FIG. 7, each assay device 400, 500 includes the substrate 40 having the upper surface 44 supporting the dual reagent areas 460, 464, the narrowed flow channel 474 including the detection zone 484 and the receiving or wicking area 480, each disposed along a fluid flow path. For purposes of this comparison, the sample receiving area 548 of the assay device 500 is defined by a conventional sample receiving area 548 that is considerably larger than that of the adjacent assay device 400.

As a result, the width dimension of the sample receiving area 448 can be tailored to be narrower, wider or essentially equal to the width of the flow channel 474. To ensure proper flow along the defined fluid flow path of the assay device 400, the width dimension of the sample receiving zone 448 is preferably slightly larger than the corresponding width dimension of the flow channel 474, but not too wide so as to create sample waste. Ratios of about 1:1 to about 3:1 are preferred. According to this specific embodiment, the sample receiving zone 448 is about 2 mm in width as compared to the flow channel 474 having a width dimension of about 1 mm. A considerably smaller sample volume is required to conduct assays in the assay device 400. In the assay device 500, a sample volume of about 1.8 microliters is required while the assay device 400 requires a volume of about 0.4 microliters, given the control to prevent pinning of sample and the ability to control flow volumes based on the peripheral reservoir 425. In order ensure fluid flow through the device 400, a portion of the sample receiving area 448 must always be disposed beneath the peripheral reservoir 425 and more specifically the meniscus 220 to insure sample in the reservoir 425 is in contact with the sample receiving area 448.

The shape of the sample receiving area 448 can be controlled in order to facilitate flow along a defined fluid flow path of the assay device 400. In addition and according to another embodiment, a plurality of sample receiving zones (not shown) can be disposed in various directions extending away from the sample addition zone and contact portion 417. These sample receiving zones can be constructed with different shapes and dimensions as compared to a conventional sample receiving zone 548, thereby enabling flow characteristics to be controlled with greater accuracy and in which a smaller amount of fluid sample is required to perform each assay(s).

Figure 8:
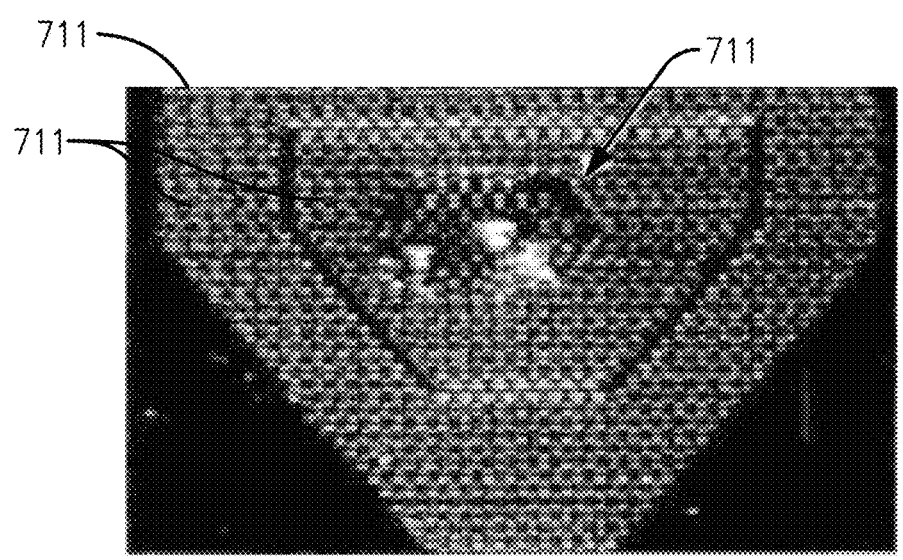
FIG. 8 is a top plan view of a portion of a reagent zone of a lateral flow assay device depicting the flow characteristics of a deposited detection material.

Referring to FIG. 8, a known reagent zone 700 of a lateral flow assay device is shown having a plurality of projections 711 that are arranged in accordance with the pattern previously described according to FIG. 6, in which the projections 711 have a first predetermined center to center reciprocal spacing ("a", FIG. 6) between adjacent aligned rows of about 160 microns and a second predetermined reciprocal spacing ("b", FIG. 6) of about 85 microns, also as measured center to center between projections 711 in a single row. For purposes of this embodiment, the diameter of the projections 711 according to this exemplary embodiment vary between about 65 and 80 microns, and more preferably the diameter of each projection 490 is about 74 microns. In addition, the height of the projections 711 is preferably in the range of about 60 to 70 microns and more preferably is about 65 microns. For the same geometry and spacings, a fluid droplet 718 of deposited detection material engaging the matrix of projections 711 tends to form a substantially hexagonal shape. Upon deposition, the detection material 718 is dried until acted upon by a moving sample front (not shown), advancing under capillary action from the sample receiving area (not shown) of the assay device.

Also and as shown in FIG. 8, the reagent area is further defined by a peripheral groove entirely surrounding the reagent area 700. The purpose of this groove is to assist in containing the deposited material and to prevent spreading beyond the predefined region.

Based on this arrangement and subsequent formation of detection material, at least three (3) issues are presented. First and though the deposited detection material 718 forms a substantially hexagonal shape, there is a need to more uniformly contain the deposited detection material into a consistent regular shape instead of a random pattern. Second, the groove around the reagent zone 700, which is designed to contain the deposited detection material, is not conducive to uniform dissolution when the sample front advances through the reagent zone 700 leading to inconsistency and inefficiencies in the use of the assay device. Third, a delay in the wetting and dissolution of the deposited detection material can result in pre-binding of sample analyte in the case of a competitive assay. This pre-binding will reduce the amount of binding of competing detection conjugate, which would result in an inaccurate assay result.

Figure 9:
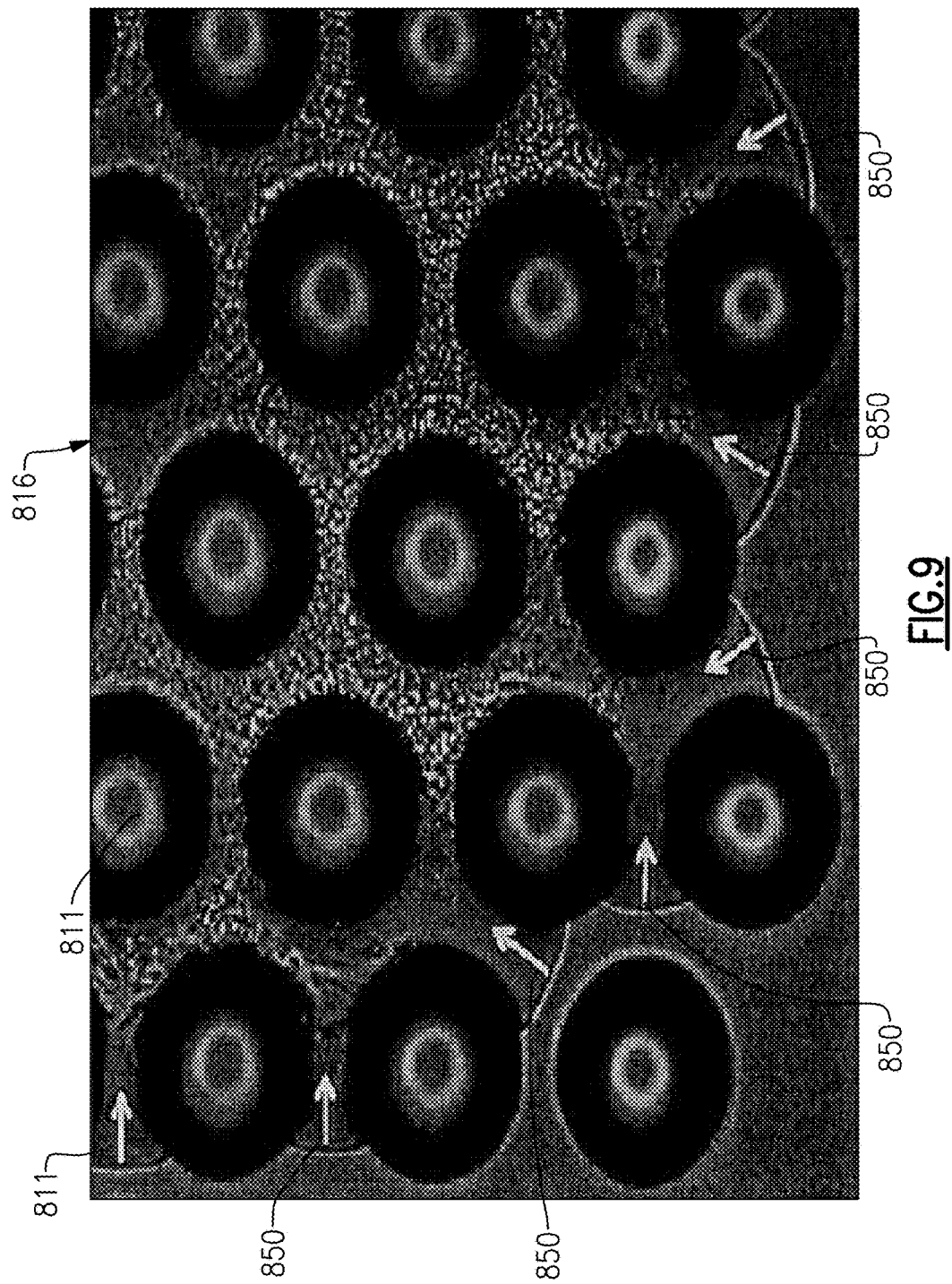
FIG. 9 is a partial top view of a portion of the reagent zone of FIG. 8, depicting the dynamics of fluid therein.
Figure 10:
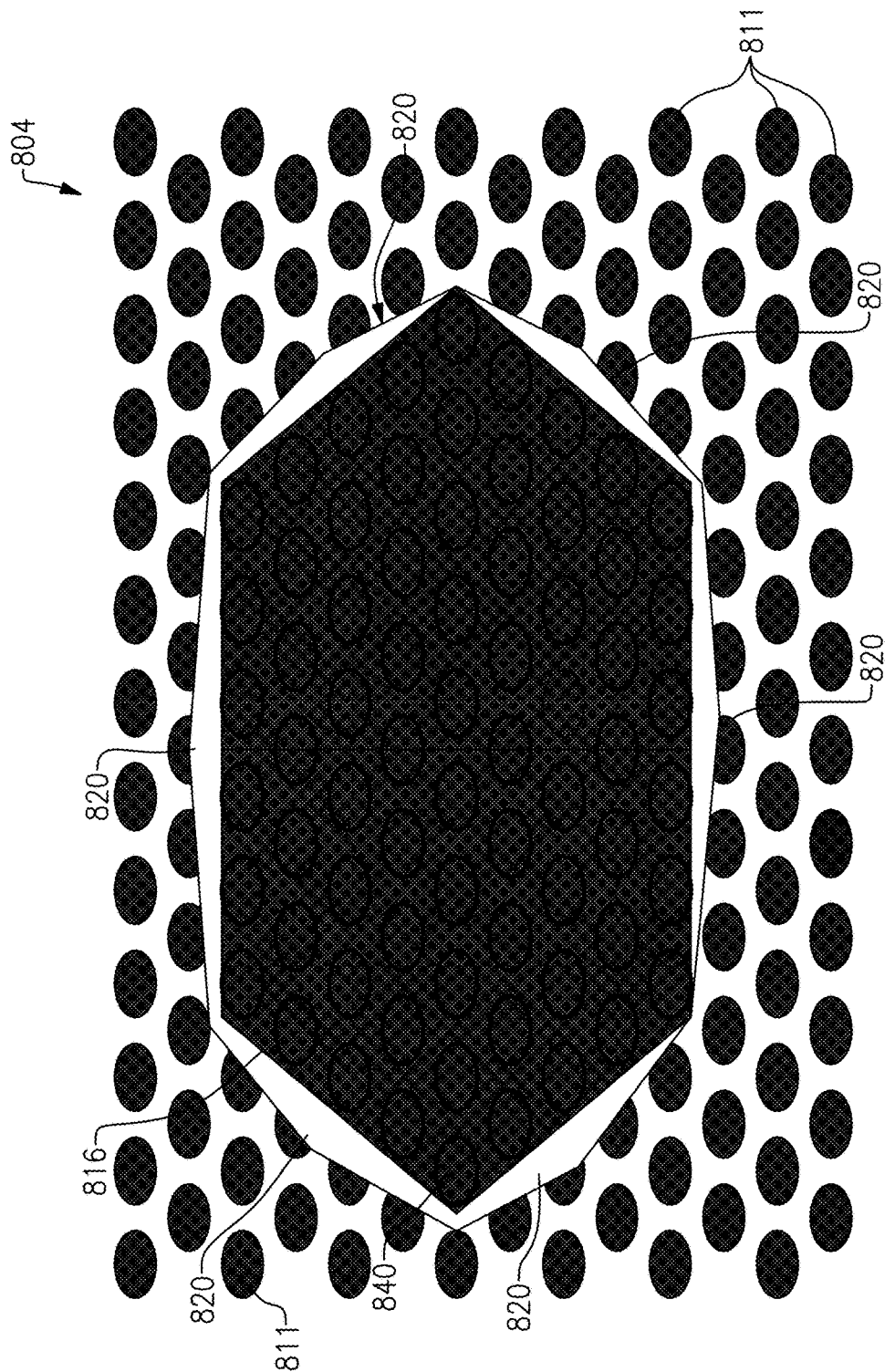
FIG. 10 is a schematic representation of the reagent zone of the lateral flow assay device of FIGS. 8 and 9.
Figure 11:
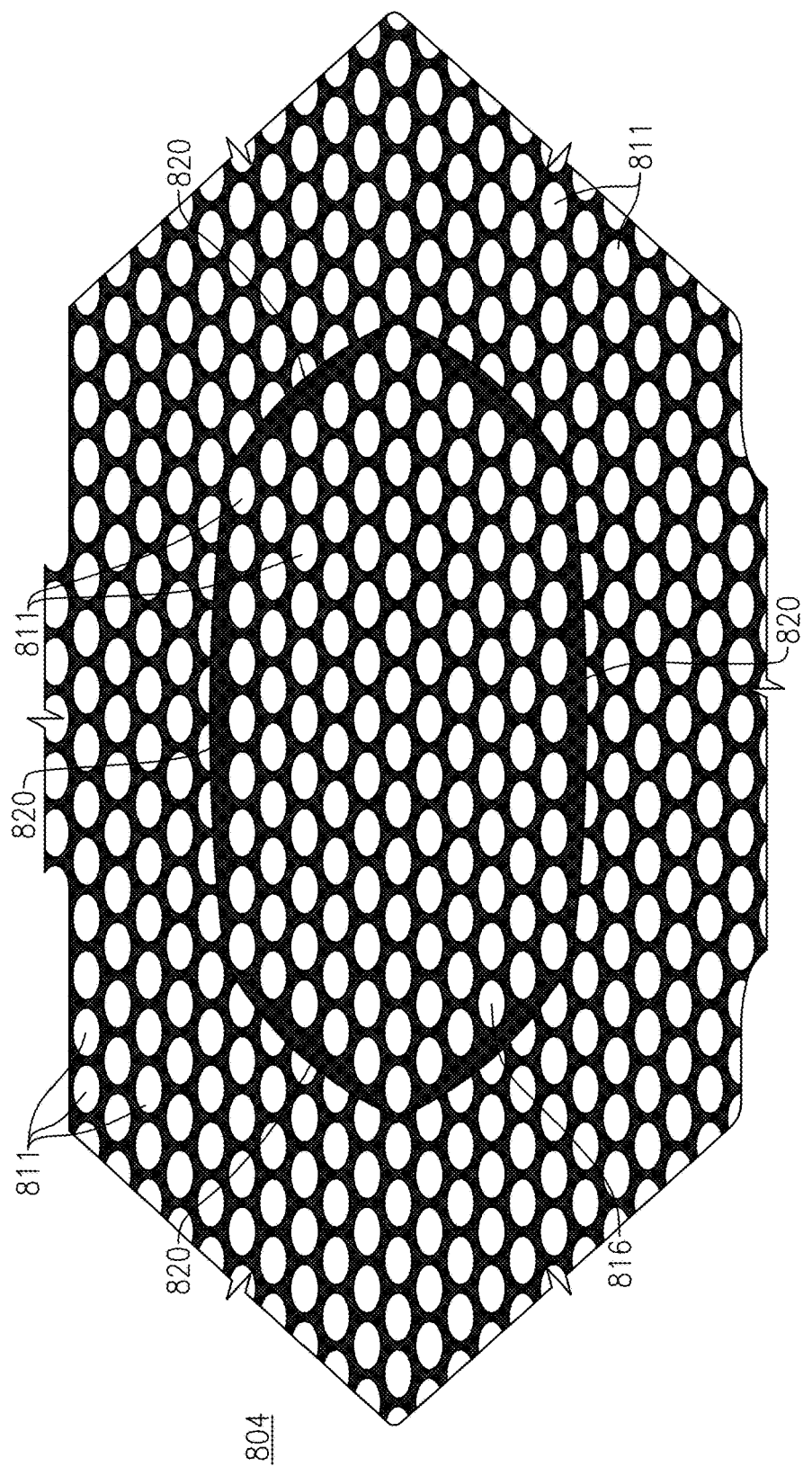
FIG. 11 is a top plan view of the reagent zone of FIGS. 8-10.

To alleviate the above-noted issues, reference is made to FIGS. 9-11, relating to a reagent zone 804 of a lateral flow assay device 800 made in accordance with another exemplary embodiment.

Referring specifically to FIGS. 10 and 11, the reagent zone 804 is defined by a plurality of projections 811 arranged in a predetermined pattern similar to that shown in FIG. 6, the pattern being defined by a series of staggered rows and predetermined spacings between aligned rows as well as center to center spacings between projections in each defined row. The reagent zone 804 is defined by a substantially hexagonal shaped area 816 with a series of edge grooves 820 that are entirely defined about the periphery thereof.

These edge grooves 820 assist to contain the deposited liquid detection material 840, FIG. 10, within the defined hexagonal area 816. The projections 811 according to this device version are defined by a substantially cylindrical configuration. A portion of the projections 811 are shown in FIG. 9 better illustrating the creation of various menisci there between, which creates backpressure, as depicted by arrows 850. These areas restrict fluid spreading and as a result each of the edge grooves 820 are influenced by the hexagonal shaped area 816. As a result, none of the projections 811 forming the hexagonal shaped area 816 are cut as part of the edge grooves 820 wherein the grooves 820 are defined by a minimum distance or spacing at the vertices of the hexagonally shaped area 816 and are at a maximum at the center of each side thereof. The application of sample 840 and the movement of the sample front to the reagent area having the detection material applied based upon this configuration does not, however, effect even dissolution of the applied material. As a result, the projections 811 are cut in the manner shown in FIGS. 10 and 11 to enable edge erosion/dissolution of the detection material. Having no cuts on the vertices (corners of the area 816) enables easier wetting of sample fluid to wet the dried detection material and produce more uniform dissolution.

Figure 12:
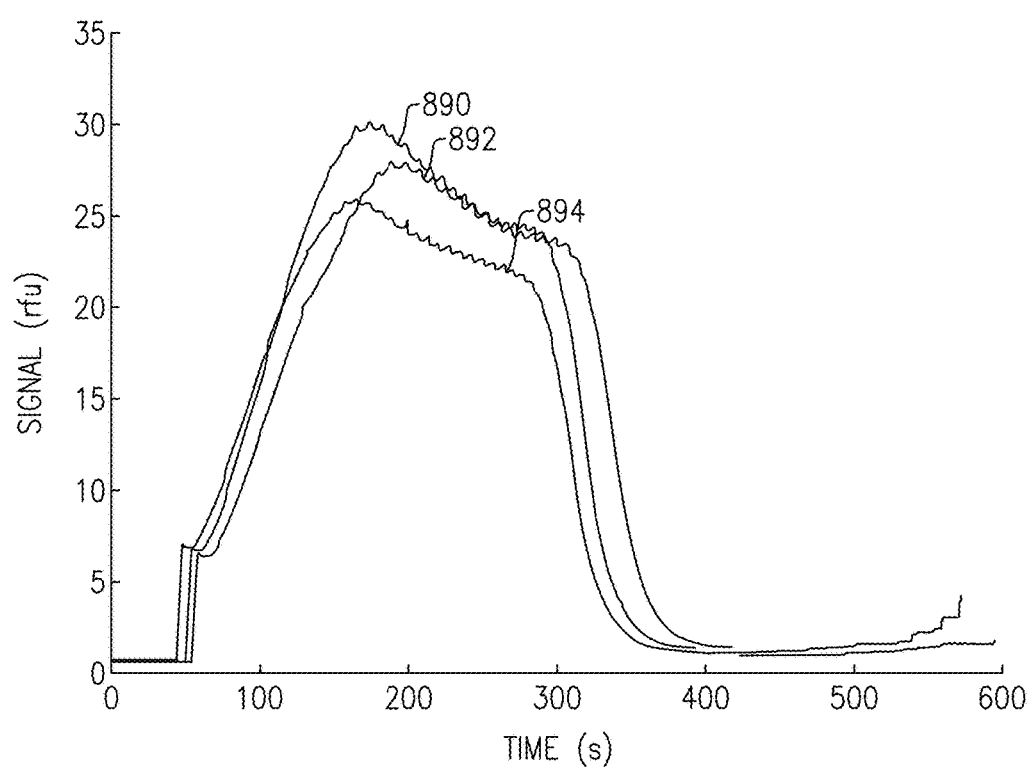
FIG. 12 is a graphical depiction of a conjugate dissolution profile for a lateral flow assay device having the reagent zone of FIGS. 8-11.

Dissolution profiles 890, 892, 894 are illustrated based on perceived signal over time in FIG. 12, showing repeatability and uniformity for a plurality of test devices with a nearly linear increase in the that amount of dissolved detection material in the early most phases of dissolution. The dissolved material amount remains at an elevated level and then drops rapidly at a later phase of dissolution.

Figure 4:
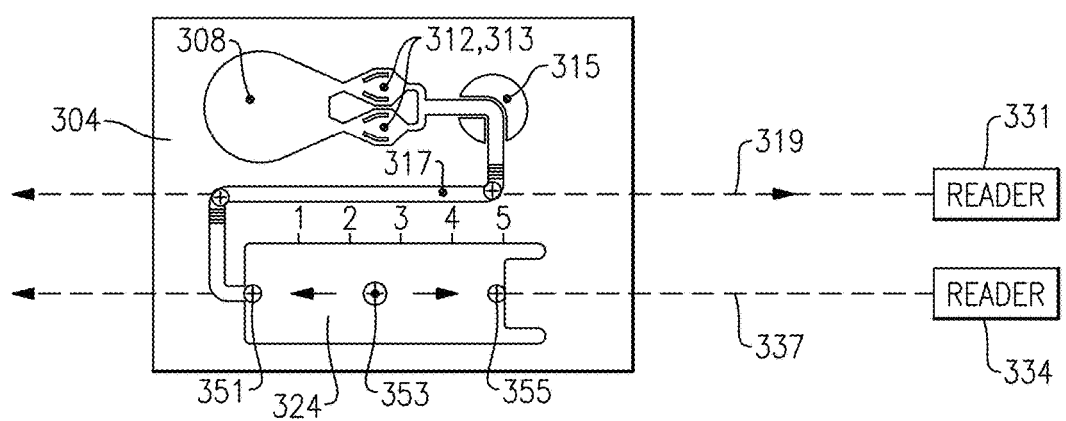
FIG. 4 is a top plan view of still another known lateral flow assay device.
Figure 13:
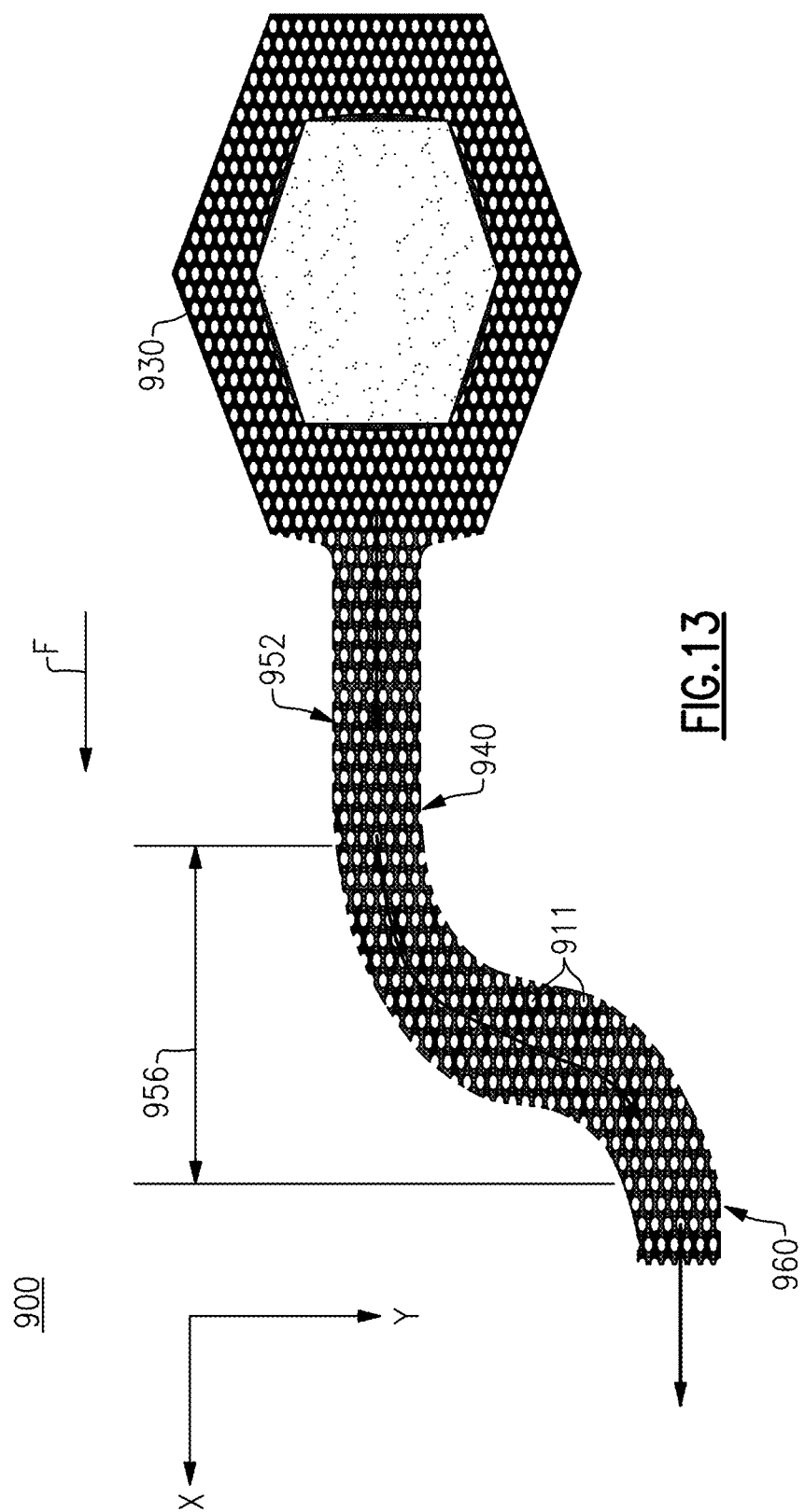
FIG. 13 is top view of a lateral flow assay device, including a flow channel having a mixing area which is made in accordance with another exemplary embodiment.

Versions of lateral flow assay devices, such as shown in FIGS. 4 and 7 include dual parallel reagent areas that are redirected by merging flow channels into a single flow channel that further extends to the detection and absorbing zones of the assay device. A concern is that there is insufficient mixing between the reagent and the sample material prior to fluid arriving at the detection zone. Referring to FIG. 13, there is shown a portion of a lateral flow assay device 900, which is made in accordance with yet another exemplary embodiment. According to this embodiment, a flow channel 940 extends from a reagent area or zone 930 of the assay device 900. The reagent zone 930 of this device 900 is downstream from a sample receiving zone (not shown) and includes a deposited or otherwise applied detection material, such as a detection conjugate, that mixes with the sample. The mixture of dissolved detection material and sample are then moved, preferably under capillary force to an entrance region 952 of the flow channel 940. This flow channel 940 can be designed as a merging flow channel, such as those depicted in FIGS. 1 and 4 extending from one of a multiple number of reagent areas and connecting into a common flow channel or can relate to a varied form of a flow channel extending between a single reagent zone and an absorbing zone (not shown) of the assay device 900. More specifically, the flow channel 940 includes the entrance portion 952 as well as an exit portion 960 on opposing ends of the channel 940 and an intermediate mixing area or portion 956.

The flow channel 930 is made up of a plurality of projections 911 extending upwardly from a top surface of the substrate (not shown) of the device 900. These projections 911 are suitably dimensioned and spaced in relation to one another to enable spontaneous lateral capillary flow of a sample received in the entrance portion 952 of the channel 940 moving in the direction F, as shown. An optional cover (not shown) can be included with the herein described assay device 900. However, the cover is not configured to significantly contribute to any capillary force moving the fluid along at least one defined fluid flow path of the assay device 900, including along the flow channel 930. That is, a predetermined spacing is not required between the top surface of the substrate or the top of the projections 911 and the cover (not shown) in order to create capillary pressure/force for sample applied to the herein described lateral flow assay device 900 and more specifically, the flow channel 940.

According to this embodiment, the projections 911 are disposed according to a predetermined pattern. This predetermined pattern is similar to that described according to FIG. 6 in which the projections 911 are aligned in spaced rows (extending in the "Y" direction, as depicted) that are staggered between adjacent rows by about one half a diameter of the projections 911 and with the first and third rows being fully aligned with each other. The diameter of the projections 911 according to this exemplary embodiment in the flow channel 940 vary between about 65 and 80 microns, and more preferably the diameter of each projection 911 is about 74 microns. In addition, the height of the projections 911 is preferably in the range of about 60 to 70 microns.

The shape/geometry and relative spacings of the projections 911 are varied between the entrance and exit portions 952, 960 and the mixing portion 956 of the flow channel 940. Each of the entrance and exit portions 952, 960 are defined by substantially linear sections having parallel rows of projections 911 having a first predetermined spacing ("a", FIG. 6) between aligned rows (measured center to center) of about 160 microns and a second predetermined spacing ("b", FIG. 6) between adjacent projections 911 of about 85 microns. In addition, each row of the these portions 952, 960 of the flow channel 930 commonly comprise about 6-7 projections extending along the "Y" direction as depicted.

The mixing zone 956 is defined, according to this exemplary embodiment, by a serpentine and substantially S-shaped configuration that is occupied by the spaced projections 911. The number of projections 911, which are also arranged in parallel rows extending in the "Y" direction, as depicted, is varied in the mixing zone 956. More specifically and according to this embodiment, the number of projections 911 extending along the "Y" direction can vary between 7 at the beginning and end of the mixing zone and about 19 or 20 at the center of the span of the mixing zone which further defines the extent of the bend of the defined serpentine configuration. In spite of the bending of the flow channel 940 and more specifically the mixing zone 956, the width (the shortest distance edge to edge) of the mixing zone 956 is almost the same (0.5 mm) across the entire length of the flow channel 950 and consonant with the width dimension of the entrance and exit portions 952, 960.

To effectuate mixing, the reciprocal spacing between the projections 911 in the mixing zone 956 is also varied in the mixing area wherein the predetermined center to center spacing "a", FIG. 6, between aligned rows of projections 911 is made larger than the corresponding center to center spacing between adjacent projections in any specific row (predetermined spacing "b", FIG. 6). In this specific embodiment, the predetermined spacing 'a', FIG. 6, between centers of projections 911 is about 180 to 200 microns between aligned rows and more preferably about 185 microns and the predetermined center to center spacing 'b', FIG. 6, is between about 80 and 90 microns between projections 911 in a single row and preferably about 85 microns, measured between the centers of adjacent projections 911 within the row. This variation in spacing induces fluidic flow between the defined rows in the direction of the row (the "Y" direction) before flow resumes between adjacent rows (the "X" direction).

More specifically, this spaced configuration of the projections 911 creates preferred flow paths for fluid entering the flow channel 940, and more specifically the mixing area 956. As the fluid passes through the projections 911 in the first row of the mixing area 956, the larger spacing "a" between the aligned rows 185 microns/2=92.5 microns versus the spacing "b" between the adjacent projections in a row of projections 911 creates a preferred fluid path in the transverse direction of the assay device 900 relative to the defined fluid flow path along the bending channel 940. The fluid moving downstream then encounters the next adjacent row of projections 911 in the mixing area 956 and behaves similarly, thereby creating flow in both planar ("X" and "Y") directions and promoting a mixing effect. The net effect produced by this design is varying flow velocities in both the X and Y directions, as fluidic sample flows through the mixing area 956 of the flow channel 950 between the entrance and exit sections, 952 and 960, thereby promoting the overall mixing effect of sample and reagent.

Figure 14:
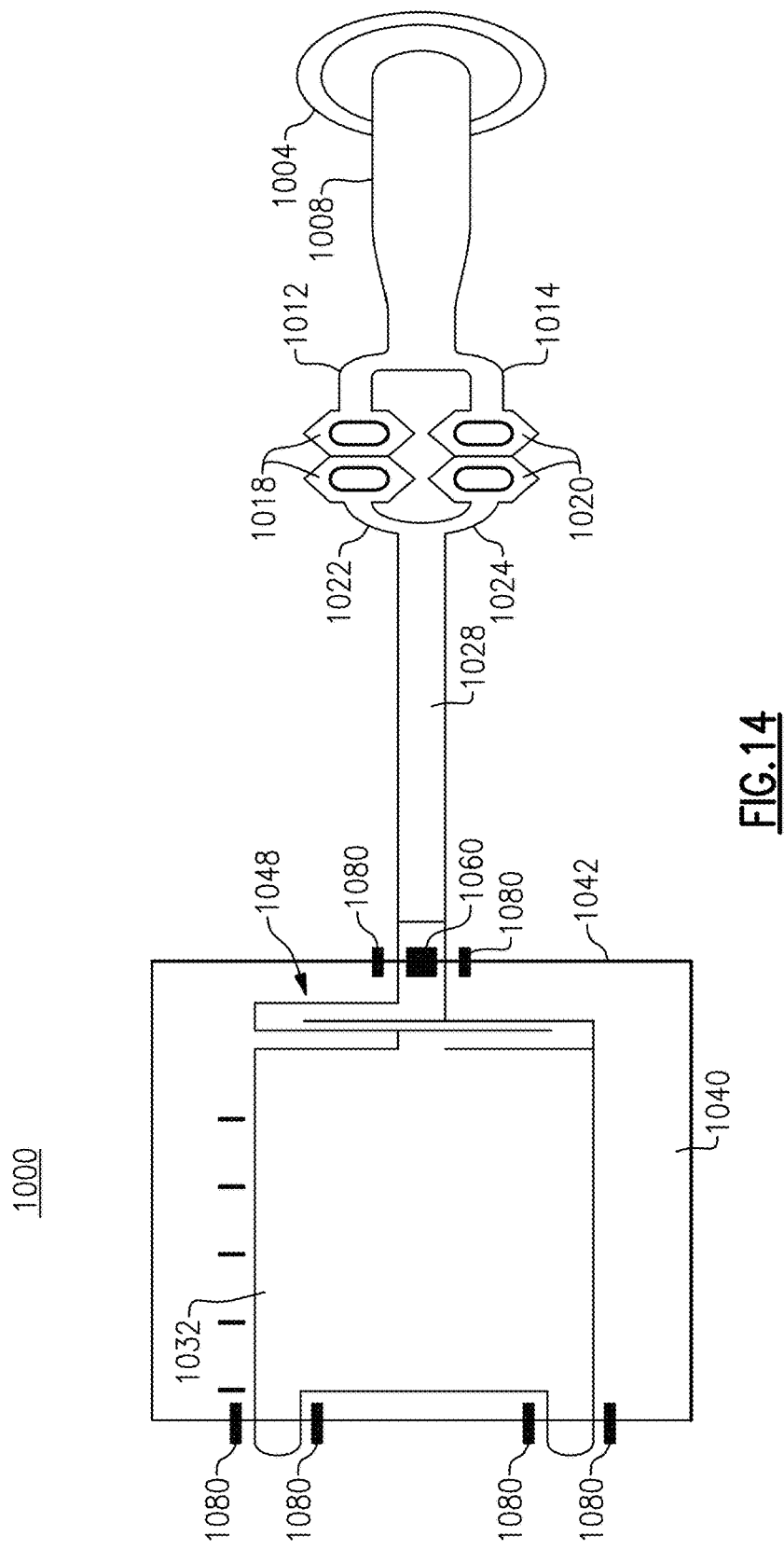
FIG. 14 is a top view of an absorbing zone of a lateral flow assay device made in accordance with another exemplary embodiment.
Figure 15:
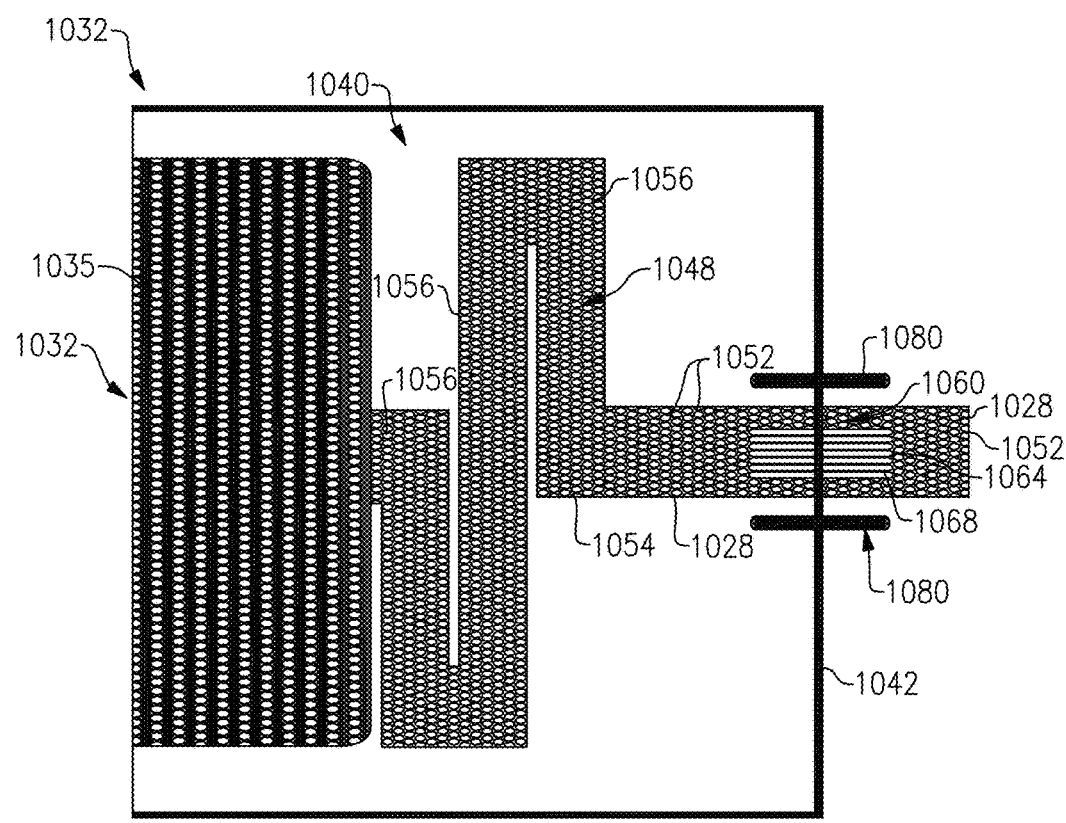
FIG. 15 is an enlarged view of the entrance of the absorbing zone of FIG. 14, depicting a flow restrictor and a flow promoting feature.
Figure 16:
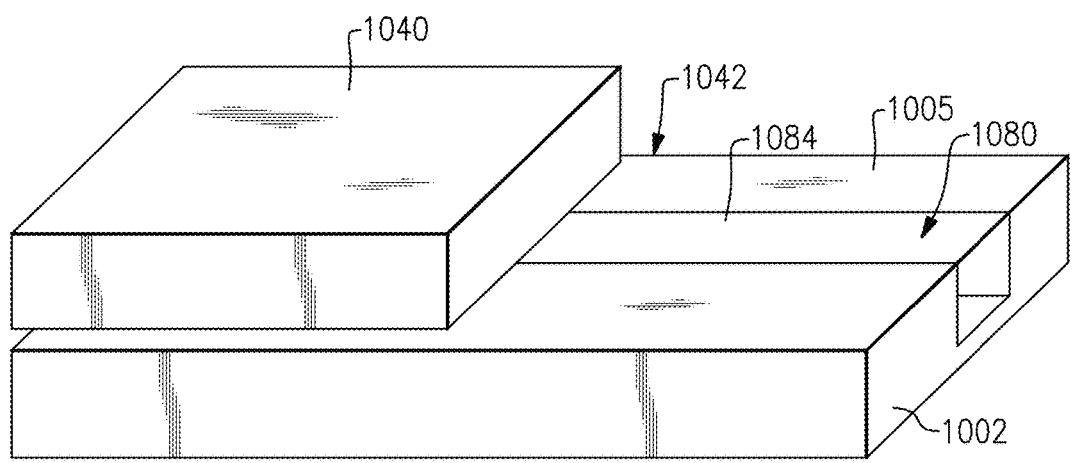
FIG. 16 is a perspective view of a portion of the flow promoting feature of FIG. 15.

Referring to FIGS. 14-16 and in accordance with another exemplary embodiment, a lateral flow assay device 1000 is herein described. The assay device 1000 according to this embodiment is defined by a substrate 1002, labeled only in FIG. 16, that is preferably made from a nonporous material, such as plastic, and is defined by a top surface 1005, also only labeled in FIG. 16. A plurality of areas or zones are disposed along a defined fluid flow path extending along the top surface 1005 of the substrate 1002. More specifically, a peripheral reservoir 1004 is provided in a sample addition area analogous to that depicted in FIG. 5 and as described previously, wherein a sample receiving zone 1008 is in contact with the peripheral reservoir 1004 and configured to pull liquid therefrom under capillary force, but without collapsing the peripheral reservoir 1004. The sample receiving zone 1008 according to this embodiment diverges into two separate flow channels 1012, 1014, that extend further into pairs of parallel disposed reagent areas 1018, 1020, respectively, with flow channels 1022, 1024 emerging downstream from the reagent areas 1018, 1020 that merge or splice into a single narrowed flow channel 1028. The narrowed flow channel 1028 includes at least one detection area (not shown) and extends linearly to an absorbing or wicking zone 1032 at the opposing end of the fluid flow path relative to the sample receiving zone 1008.

Each of the disposed zones, according to this exemplary embodiment, include flow control elements in the form of projections 1052, FIG. 15, that are configured to move fluid along the defined fluid flow path from the sample receiving area 1008 to the absorbing zone 1032 by inducing capillary force to an applied liquid. A hydrophilic foil or tape cover 1040 spans and covers the entire absorbing zone 1032, the cover 1040 having a peripheral outer edge 1042 extending over the flow channel 1028 at or proximate the entrance to the absorbing zone 1032. In one version, the hydrophilic foil cover 1042 can be adhesively attached/secured to the top of the projections 1035 in which the foil cover 1042 and/or the adhesive used to secure the cover 1040 can be hydrophilic. The function of the hydrophilic foil cover 1040 is to minimize the effects of evaporation of the projections 1035 of the absorbing zone 1032 to the environment, in addition to supplementing the capillary force.

As previously discussed herein, the use of a smaller sample receiving zone 1008 requires a smaller total aliquot of sample in order to conduct the assay. If smaller fluid samples are used in the lateral flow assay device 1000, less time is taken to move all of the fluid and detection material from the reagent areas 1018, 1020 to the absorbing zone 1032. Therefore and when using smaller fluidic volumes, the absorbing zone 1032 can be made much smaller. There is, however, a competing concern relating to the total time that is still required to conduct the assay. As a result, there is a need to delay the flow rate of sample for assays having longer reaction times and in some instances to allow for better wash of the detection zone(s) of the assay device.

According to the exemplary embodiment and as shown in FIGS. 14 and 15, a flow restrictor 1048 can be disposed within the wicking zone 1032 and bridge the projections 1035 and the flow channel 1028. In this exemplary and depicted embodiment, the flow restrictor 1048 is defined by a folding channel 1054 comprising a plurality of overlapping segments 1056 that extend transversely in a back and forth configuration relative to the flow channel 1028, the segments 1056 extending across the width dimension of the absorbing zone 1032 and terminating at the projections 1035 of the absorbing zone 1032. The projections 1052 are defined by relative dimensions (i.e., heights and diameters), as well as reciprocal center to center spacing between the projections 1052 that enable capillary pressure to be applied to an introduced fluidic sample. The flow restrictor 1048 is designed to add significant flow resistance, while preferably having a fairly compact footprint so as not to assume large sections of the assay device 1000. According to this exemplary embodiment, the folding channel 1054, including each of the segments 1056 defining the flow restrictor 1048, has an overall width dimension of about 0.5 mm and in which the projections 1052 are arranged in a manner similar to that illustrated in FIG. 6, the projections 1052 having predetermined spacings of about 160 microns as measured center to center between aligned rows in the length dimension of the flow channel 1054 and about 85 microns as measured center to center between adjacent projections 1052 in the width dimension of each row.

In operation, the flow restrictor 1048 can delay the flow of sample and dissolved detection material over time as compared to a device design that does not include the flow restrictor 1060. According to one example, a lateral flow assay device having a flow restrictor of the above design created a delay of over 2 minutes and 46 seconds for a 10-15 minute assay as opposed to a lateral flow device having an absorbing area that is not equipped with a flow restrictor.

The total length of the flow restrictor 1048 according to this embodiment is about 14 mm, although this parameter also can be easily varied. In operation, the flow restrictor 1048 is configured to add significant flow resistance, while taking up a relatively small area of the absorbing zone 1032 of the herein described lateral flow device 1000.

Additionally, the presence of the hydrophilic tape cover 1040 and more specifically the relatively sharp outer peripheral edge 1042 can create issues in regard to the lateral flow assay device 1000. First, the cover 1040 can potentially create fluid stoppage at the entrance of the absorbing zone 1032 with regard to the flow channel 1028 as fluid advances past the edge 1042. Referring to FIGS. 14 and 15 and accordance with the exemplary embodiment, a feature can be provided to facilitate fluidic flow into the absorbing zone 1032 in the form of a flow promoting or bridging structure 1060. According to this exemplary embodiment and referring to FIGS. 15 and 16, the flow bridging structure 1060 comprises at least one groove 1064 and/or bar 1068 formed in the top surface 1002 of the substrate 1002, the flow bridging structure 1060 being provided at the entrance of the absorbing zone 1032 and preferably in substantially the center of the flow channel 1028, the bridging structure being surrounded by the projections 1052. The flow bridging structure 1060 commences upstream from the outer edge 1042 of the foil cover 1040 and extends downstream of the outer edge 1042 and within the absorbing zone 1032 beneath the foil cover 1040.

According to the herein described embodiment, a plurality of grooves 1064 and intermediate bars 1068 form the flow bridging structure 1060. However, there are variations and modifications that can be made. For example and according to one version, a single bar (not shown) can be provided to serve as a suitable bridging structure to enable fluidic flow in spite of the presence of the outer edge 1042 of the hydrophilic foil cover 1040.

In addition, the presence of the outer edge 1042 of the hydrophilic foil cover 1040 may also cause undesired wicking along the periphery of the foil cover 1040 either as fluid enters the absorbing zone 1032 or after the projections 1035 of the absorbing zone 1032 have been filled with incoming fluid. This wicking could affect test results if fluid were permitted to back flow in relation to the detection zone (not shown) of the device 1000. Therefore and in order to minimize such an undesired effect according to the exemplary embodiment, a series of parallel grooves 1080 are provided, the grooves 1080 extending transverse to the edge of the foil cover 1040 and having a length that extends on each side of the edge. According to this embodiment and as depicted in FIGS. 15 and 16, a plurality of grooves 1080 are provided adjacent the flow channel 1028 and also in spaced relation at the opposing end of the absorbing zone 1032. The grooves 1080, each having distinct (sharp) edges 1084, shown particularly in FIG. 16, can prevent fluid wicking along the outer edge 1042 of the tape cover 1040. One major advantage is to use the parallel groove 1080 to make the tape cover 1040 more consistently attach to the top of the bar and to allow fluid to easily flow through the projections 1054 and 1035.

Wicking along the edge of the hydrophilic tape cover 1040 can occur since both the edge 1042 and the top substrate surface 1005 are hydrophilic in nature and create a geometry therebetween that can produce a capillary pressure or force that may drive unwanted fluid flow outside the defined fluid flow path. The sharp edge 1084 of the formed groove(s) 1080, however, creates an energy barrier to locally stop the wicking flow along the edge of the substrate 1002.

Advantageously, the foregoing structure and features added to the absorbing zone 1032 of the herein described lateral flow assay device 1000 provides more robust flow of sample with reduced flow stoppage at the end of the hydrophilic tape cover 1040, wherein wicking is enabled to occur relative to the absorbing zone 1032 of the herein described lateral flow assay device 900.

PARTS LIST FOR FIGS. 1-16

1 lateral flow assay device
2 sample addition area or zone
3 reagent area or zone
4 flow channel
5 wicking or absorbing area or zone
7 top surface, substrate
12 projections
20 lateral flow assay device 40 substrate, planar
44 top or upper surface
48 sample receiving area or zone
52 reagent area or zone
56 detection area
57 flow bridging structure
60 wicking or absorbing area or zone
64 flow channel
70 hydrophilic foil layer
72 vent areas
100 lateral flow assay device
104 substrate
108 sample addition area or zone
112 reagent area or zone
116 flow channel
120 wicking (absorbing) area
124 reagent addition zone
130 hydrophilic foil layer
205 sample
210 aperture
214 bottom surface, filter
215 filter
220 meniscus
235 welding groove
240 cover or lid
300 lateral flow assay device
304 substrate, planar
308 sample addition area or zone
312 reagent area or zone
313 reagent area or zone
315 reagent addition zone
317 flow channel
319 axis
324 wicking or absorbing area or zone
331 first reader apparatus
334 second reader apparatus
337 axis
351 detection area
353 detection area
355 detection area
400 lateral flow assay device
417 contact area, filter
420 filtrate
422 residue
425 peripheral reservoir
427 contact portion or area
429 extending portion, filter
448 sample receiving zone
456 flow channel (split)
457 flow channel (split)
460 reagent zone or area
464 reagent zone or area
468 flow channel (splice)
470 flow channel (splice)
474 flow channel
480 wicking or receiving zone
484 detection area(s) or zone(s)
490 projections
492 row, projections
494 row, projections
496 row, projections
600 lateral flow assay device
604 substrate
608 top surface
611 microposts
618 sample receiving area
630 detection area
700 reagent zone
711 projections
718 droplet of detection material (forming a hexagonal configuration)
800 lateral flow assay device
804 reagent area
811 projections
816 hexagonal shaped area
820 edge grooves
840 sample
850 menisci
890 dissolution profile
892 dissolution profile
894 dissolution profile
900 lateral flow assay device
911 projections
930 reagent zone
934 conjugate area
952 entrance section
956 mixing area or region
960 exit section
1000 lateral flow assay device
1002 substrate
1004 peripheral reservoir
1005 top surface
1008 sample receiving zone
1012 spliced flow channel
1014 spliced flow channel
1018 reagent zones
1020 reagent zones
1022 merged flow channel
1024 merged flow channel
1028 flow channel
1032 absorbing or wicking zone
1035 projections, absorbing or wicking zone
1040 hydrophilic foil cover
1042 outer edge, foil cover
1048 flow restrictor
1052 projections
1054 flow channel
1056 segments
1060 flow promoting or bridging structure
1064 grooves
1068 bars
1080 grooves
1084 edge, groove It will be readily apparent that other variations and modifications can be made in accordance with the inventive concepts discussed herein as well as according to the following claims. In addition, separate references are made throughout to "an embodiment" or "an exemplary embodiment" or "a specific embodiment". These references do not necessarily refer to the same embodiment or embodiments; however, such embodiments are also not mutually exclusive, meaning that the features described throughout as pertaining to the various zones of the herein described device can be combined in various permutations to include some or all of the embodiments.

We claim:

1. A lateral flow assay device comprising:
a non-porous substrate having a top surface;
a sample addition area including a cover having an aperture and a filter peripherally supported within the aperture configured for adding a sample fluid, the cover being disposed above the substrate and defining a spacing therebetween, the supported filter including a portion in direct contact with the top surface of the substrate, in which the filter includes a surface section extending between the portion directly contacting the substrate and a supporting edge of the cover aperture, said surface section forming an angle α with the top surface of the substrate, and creating a peripheral reservoir of sample fluid that passes through the filter, said peripheral reservoir being retained by capillary forces between the filter and the substrate that retains a volume of fluid sample; and a sample receiving zone extending along a portion of the substrate and into contact with only a portion of the peripheral reservoir, the sample receiving zone being defined by a plurality of projections extending from the top surface of the substrate, the plurality of projections having dimensions and reciprocal spacing that creates lateral capillary pressure for drawing fluid from said peripheral reservoir without disturbing the integrity of the reservoir.

2. The lateral flow assay device of claim 1, wherein the sample receiving zone is disposed along a fluid flow path of the assay device, said assay device further including at least one reagent zone and an absorbing zone each disposed along the fluid flow path.

3. The lateral flow assay device of claim 1, in which the angle α is greater than zero.

4. The lateral flow assay device of claim 1, wherein the angle α is about 10 degrees.

5. The lateral flow assay device of claim 1, including a plurality of sample receiving zones interconnecting with separate portions of the peripheral reservoir and extending in different planar directions therefrom.

6. The lateral flow assay device of claim 2, wherein the fluid flow path further comprises a flow channel interconnecting the reagent zone, the detection zone and the absorbing zone and in which the sample receiving zone has an overall width dimension that is larger than the width dimension that is between about one and three times the width dimension of the flow channel.

7. The lateral flow assay device of claim 6, in which the width dimension of the sample receiving zone is two times the width dimension of the flow channel.

8. The lateral flow assay device of claim 7, wherein the width dimension of the flow channel is between about 0.5 and 1.5 mm.

* * * * *